United States Patent
Nuijens et al.

(10) Patent No.: US 10,920,258 B2
(45) Date of Patent: *Feb. 16, 2021

(54) CHEMO-ENZYMATIC SYNTHESIS OF SEMAGLUTIDE, LIRAGLUTIDE AND GLP-1

(71) Applicant: ENZYPEP B.V., Geleen (NL)

(72) Inventors: Timo Nuijens, Geleen (NL); Ana Toplak, Geleen (NL); Peter Jan Leonard Mario Quaedflieg, Geleen (NL)

(73) Assignee: ENZYPEP B.V., Geleen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/783,570

(22) Filed: Feb. 6, 2020

(65) Prior Publication Data
US 2020/0347427 A1 Nov. 5, 2020

Related U.S. Application Data

(63) Continuation of application No. 16/463,471, filed as application No. PCT/EP2019/056046 on Mar. 11, 2019.

(30) Foreign Application Priority Data

Mar. 9, 2018 (EP) ..................................... 18161084

(51) Int. Cl.
| | |
|---|---|
| *A61K 38/00* | (2006.01) |
| *C12P 21/02* | (2006.01) |
| *C12N 9/50* | (2006.01) |
| *C12N 9/00* | (2006.01) |

(52) U.S. Cl.
CPC ................ *C12P 21/02* (2013.01); *C12N 9/50* (2013.01); *C12N 9/93* (2013.01); *C12Y 304/21062* (2013.01)

(58) Field of Classification Search
None
See application file for complete search history.

(56) References Cited

U.S. PATENT DOCUMENTS

| | | | |
|---|---|---|---|
| 5,403,737 | A | 4/1995 | Abrahmsen |
| 6,451,974 | B1 | 9/2002 | Hansen |

FOREIGN PATENT DOCUMENTS

| WO | 0226956 | A1 | 4/2002 |
|---|---|---|---|
| WO | 2007147816 | A1 | 12/2007 |
| WO | 2014199397 | A2 | 12/2014 |
| WO | 2016046753 | A1 | 3/2016 |
| WO | 2016056913 | A1 | 4/2016 |
| WO | 2017007324 | A1 | 1/2017 |
| WO | WO-2017007324 | A1 * | 1/2017 ............ C12P 21/02 |
| WO | 2018032843 | A1 | 2/2018 |

OTHER PUBLICATIONS

International Search Report and Written Opinion for Corresponding International Application No. PCT/EP2019/055918 (14 Pages) (dated Apr. 16, 2019).
Nuijens et al., "Chemo-enzymatic peptide synthesis (CEPS) using omniligases and selective peptiligases Efficient biocatalysts for assembling linear and cyclic peptides and protein conjugates", Chimica Oggi, 2016, vol. 34, No. 6, pp. 16-19.
Nuijens et al., "Engineering a Diverse Ligase Toolbox for Peptide Segment Condensation", Adv. Synth. Catal., 2016, vol. 358, No. 24, pp. 4041-4048.
International Search Report for Corresponding International Application No. PCT/EP2019/056046(dated Apr. 12, 2019) (20 Pages).
"Mutant subtilisin BPN' protein S88P", Database Geneseq, 2002, XP002790242, 1 page.
Chang et al., "Subtiligase: A tool for semisynthesis of proteins", Proc. Natl. Acad. Sci., 1994, vol. 91, pp. 12544-12548.
Matsunaga et al., "Development of an Efficient Amino Acid Sequencing Method Using Fluorescent Edman Reagent 7•[(N, N-Dimethylamino)sulfonyl]-2,1,3-benzoxadiazol-4-yl Isothiocyanate", Anal. Chem., 1995, vol. 67, pp. 4276-4282.

* cited by examiner

*Primary Examiner* — Jeanette M Lieb
(74) *Attorney, Agent, or Firm* — Lucas & Mercanti, LLP

(57) ABSTRACT

A method for synthesizing a peptide having the sequence His-X-Glu-Gly-Thr-Phe-Thr-Ser-Asp-Val-Ser-Ser-Tyr-Leu-Glu-Gly-Gln-Ala-Ala-Y-Glu-Phe-Ile-Ala-Trp-Leu-Val-Z-Gly-Arg-Gly is disclosed. The method includes enzymatically coupling:

(a) a peptide C-terminal ester or thioester having a first peptide fragment with the sequence His-X-Glu-Gly-Thr-Phe-Thr-Ser-Asp-Val-Ser-(thio)ester; and (b) a peptide nucleophile having an N-terminally unprotected amine having a second peptide fragment with the sequence H-Ser-Tyr-Leu-Glu-Gly-Gln-Ala-Ala-Y-Glu-Phe-Ile-Ala-Trp-Leu-Val-Z-Gly-Arg-Gly;

wherein:

X is Ala or an α-amino-isobutyric acid (Aib) residue;

Y is Lys, which Lys has a free side-chain ε-amino group or of which Lys the side-chain ε-amino group is protected with a protective group or of which Lys the side-chain ε-amino group is functionalized with an amino acid or another functional group; and Z is Arg or Lys.

21 Claims, No Drawings
Specification includes a Sequence Listing.

CHEMO-ENZYMATIC SYNTHESIS OF SEMAGLUTIDE, LIRAGLUTIDE AND GLP-1

CROSS-REFERENCE TO RELATED APPLICATIONS

This application is a continuation of U.S. patent application Ser. No. 16/463,471, filed May 23, 2019, which in turn is a 371 of PCT/EP2019/056046, filed Mar. 11, 2019, which claims the benefit of European Patent Application No. 18161084.1 filed Mar. 9, 2018, the contents of each of which are incoporated herein by reference.

SEQUENCE LISTING

The sequence listing of the present application has been submitted electronically via EFS-Web as an ASCII formatted sequence listing with a file name 1310-04_Sequence-Listing.txt, creation date of Feb. 6, 2020 and a size of 17,189 bytes. The sequence listing is part of the specification and is herein incorporated by reference in its entirety.

FIELD OF THE INVENTION

The invention relates to a method wherein a peptide fragment coupling is carried out enzymatically in the presence of a ligase to synthesise a peptide comprising the sequence His-X-Glu-Gly-Thr-Phe-Thr-Ser-Asp-Val-Ser-Ser-Tyr-Leu-Glu-Gly-Gln-Ala-Ala-Y-Glu-Phe-Ile-Ala-Trp-Leu-Val-Z-Gly-Arg-Gly (SEQ ID NOS: 4-7).

BACKGROUND OF THE INVENTION

Several peptides comprising the amino acid sequence H-His-X-Glu-Gly-Thr-Phe-Thr-Ser-Asp-Val-Ser-Ser-Tyr-Leu-Glu-Gly-Gln-Ala-Ala-Y-Glu-Phe-Ile-Ala-Trp-Leu-Val-Z-Gly-Arg-Gly-OH (SEQ ID NOS: 4-7) are well known in the art as insulinotropic peptides. These peptides include GLP-1, Liraglutide and Semaglutide.

Human GLP-1 (Glucagon-like peptide-1) has the formula H-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly-OH (SEQ ID NO: 5).

Liraglutide is an Arg$^{20}$-GLP-1 analogue substituted on the ε-amino group of the lysine in position 20 of the above sequence with a Glu-spaced palmitic acid. Thus, Liraglutide has the formula H-His-Ala-Glu-Gly-Thr-Phe-Thr-Ser-Asp-Val-Ser-Ser-Tyr-Leu-Glu-Gly-Gln-Ala-Ala-Lys(Pal-γ-Glu)-Glu-Phe-Ile-Ala-Trp-Leu-Val-Arg-Gly-Arg-Gly-OH (SEQ ID NO: 6) (see also FIG. 1, all chiral amino acid residues are L-amino add residues). In Lys(Pal-γ-Glu) the ε-amino-group of the Lys residue is linked with the γ-Glu carboxylic side-chain and the Glu is N-palmitoyiated.

Semaglutide has the formula H-His-Aib-Glu-Gly-Thr-Phe-Thr-Ser-Asp-Val-Ser-Ser-Tyr-Leu-Glu-Gly-Gln-Ala-Ala-Lys(AEEA-AEEA-γ-Glu-17-carboxyheptadecanoyl)-Glu-Phe-Ile-Ala-Trp-Leu-Val-Arg-Gly-Arg-Gly-OH (SEQ ID NO: 7). Herein AEEA-AEEA-γ-Glu-17-carboxyheptadecanoyl is N-(17-carboxy-I-oxoheptadecyl)-L-γ-glutamyl-2-[2-(2-aminoethoxy)-ethoxy]acetyl-2-[2-(2-aminoethoxy) ethoxy]acetyl (see also FIG. 2, all chiral amino acid residues are L-amino acid residues).

These peptides can, e.g., be used in the treatment of diabetes II. Further, e.g., Liraglutide can be used in the treatment of obesity, as injectable adjunct to a reduced-calorie diet and increased physical activity for chronic weight management in adult patients.

Processes for synthesizing peptides, including oligopeptides like GLP-1, Liraglutide and Semaglutide, are known in the art. Methods to synthesise insulinotropic peptides, such as GLP-1 and analogues thereof are described in WO2007147816 and in WO2016/046753. In the 'BACKGROUND OF THE INVENTION' of WO2016/046753 a detailed description is given of suitable preparation methods, notably recombinant methodology, sequential synthesis on a solid support, solid phase synthesis of Liraglutide involving coupling a peptide sequence containing amino acid residues (1-10) to a sequence containing amino add residues (11-31), or solid phase synthesis of Liraglutide involving the preparation of peptide sequences containing amino acid residues (1-4), (15-16) and (17-31), coupling the peptides containing amino acid residues (15-16) with (17-31) and sequential addition of amino acids before coupling with the peptide containing amino acid sequence (1-4).

In accordance with WO2016/046753 GLP-1 peptides are prepared in a process comprising liquid or solid phase peptide synthesis or a combination thereof, wherein the process comprises a final coupling step in which at least two fragments are coupled at a terminal Gly residue, and wherein at least one of the fragments is prepared by coupling of at least two sub-fragments. Liraglutide is in particular obtained by coupling His-Ala-Glu-Gly (residues 1-4 of SEQ ID NO: 6) and Thr-Phe-Thr-Ser-Asp-Val-Ser-Ser-Tyr-Leu-Glu-Gly-Gln-Ala-Ala-Lys(Pal-Glu-OX)-Glu-Phe-Ile-Ala-Trp-Leu-Val-Arg-Gly-Arg-Gly-OH (SEQ ID NO: 8). In this sequence X represents H or a protecting group for the Glu α-carboxylic acid group.

As follows from 'BACKGROUND OF THE INVENTION' of WO2016/046753 there remains a need for discovering new methods for the synthesis of GLP-1 proteins such as Liraglutide or Semaglutide to provide a better, more efficient and/or cheaper process or to provide a product which can be more readily purified in order to achieve a product with improved yield and purity. In particular, it expresses the need to provide a method for preparing GLP-1 and analogues, such as Liraglutide or Semaglutide, especially on an industrial scale, which should not require the use of toxic or otherwise undesirable reagents in good yields and which can be readily purified to obtain a product having high purity.

An enzymatic synthesis of GLP-1 or an analogue thereof, like Liraglutide or Semaglutide is not suggested in WO2007147816 and in WO2016/046753, which both focus on chemical synthesis.

However, fully chemical synthesis of peptides has disadvantages, as also discussed in the above cited prior art. Further, peptides longer than 15 amino acids are often very difficult to synthesize on the solid phase due to side reactions. As a consequence, purification is troublesome. Therefore, peptides longer than 10 amino adds are often synthesized by a combination of solid phase synthesis of side-chain protected oligopeptide fragments which are subsequently chemically condensed in solution, e.g. as in a 10+10 condensation to make a peptide of 20 amino acids. The major drawback of chemical side-chain protected oligopeptide fragment condensation is that, upon activation of the C-terminal amino acid residue of the acyl donor, racemisation occurs. In contrast enzyme-catalyzed peptide couplings are completely devoid of racemisation and have several other advantages over chemical peptide synthesis such as the absence of side reactions on the side-chain functionalities. For industrial application, an enzymatic peptide synthesis concept based on a kinetic approach, i.e. using an acyl donor C-terminal ester is most attractive (see for instance N.

Sewald and H.-D. Jakubke, in: "Peptides: Chemistry and Biology", 1st reprint Ed. Wiley-VCH Verlag GmbH, Weinheim 2002).

A problem with enzymatic coupling in aqueous solutions is that the presence of water tends to promote hydrolysis rather than coupling. Some reports have been published on the enzymatic condensation of oligopeptide fragments in aqueous solution (Kumaran et al. Protein Science, 2000, 9, 734; Björup et al. Bioorg. Med. Chem. 1998, 6, 891; Homandberg et al. Biochemistry, 1981, 21, 3387; Komoriya et al. Int J. Pep. Prot Res. 1980, 16, 433).

It was found by Wells et al. (U.S. Pat. No. 5,403,737) that the enzymatic condensation of oligopeptides in aqueous solution could be significantly improved by altering the active site of subtilisin BPN', a subtilisin from *B. amyloliquefaciens* (SEQ ID NO: 2). When two mutations were introduced, i.e. S221C and P225A, a subtilisin BPN' variant called subtiligase was obtained having a 500-fold increased synthesis over hydrolysis ratio (S/H ratio) as compared to wild-type subtilisin BPN'. In further experiments, Wells et al. added five additional mutations to subtiligase to make the enzyme more stable (Proc. Natl. Acad. Sci. USA, 1994, 91, 12544). The new mutant called stabiligase appeared moderately more resistant to sodium dodecasulphate and guanidinium hydrochloride, but hydrolysis was still a major side reaction.

In WO 2016/056913 a solution is provided for the undesirably high hydrolytic activity encountered with enzymes like subtiligase or stabiligase when used for (oligo)peptide synthesis in an aqueous environment by providing subtilisin BPN' variants or a homologues thereof, with specific mutations. These variants or homologues are in particular suitable to catalyzed the synthesis of peptides by coupling a first peptide fragment and a second peptide fragment wherein the first fragment is a peptide C-terminal ester or thioester and the second fragment is a peptide nucleophile having an N-terminally unprotected amine.

The inventors considered to apply enzymatic fragment condensation for the synthesis of GLP-1, Liraglutide and Semaglutide starting from peptide fragments mentioned in WO2007147816 or WO2016/046753. Amongst others, the inventors considered to couple the 10-mer peptide having amino acid residues 1-10 to the 21-mer peptide containing amino acid residues 11-31 of Liraglutide, Semaglutide or GLP-1 by enzymatic fragment condensation, with the 10-mer as the (thio)ester and the 21-mer as the nucleophile. For the coupling of the peptide C-terminal (thio)ester having amino acid residues 1-10 to a peptide nucleophile containing amino acid residues 11-31, the presence of a serine at both P1' and P2' was found to be a disadvantage for the peptide nucleophile. Further possible reasons for a lack of effective coupling could be the presence of a non-hydrophobic amino acid at P4 (threonine) of the peptide C-terminal (thio)ester. Further, the inventors attempted to couple a peptide C-terminal (thio)ester having amino add residues 1-4 to a peptide nucleophile containing amino acid residues 5-31, without success. The inventors concluded that in particular the presence of histidine at P4 and/or the presence of glycine at P1 of the peptide C-terminal (thio)ester are detrimental to effective coupling. As illustrated in Examples 1 and 2 of present disclosure, it was found that it is possible to prepare these peptides by enzymatic coupling in the presence of a ligase, also in an aqueous reaction medium, but that the yield was unexpectedly low for several processes designed on the basis of scientific considerations, such as the consideration that a ligase like a subtilisin variant or homologue thereof favours coupling of C-terminal peptide (thio)esters that have a hydrophobic amino acid residue at the P4 position (the fourth amino acid from the C-terminal end) of the peptide C-terminal ester or thioester. Amongst others, a method was carried out wherein the peptide with the amino acid sequence of Liraglutide ('H-Liraglutide-1-31-OH') was prepared by enzymatically coupling the 13-mer C-terminal ester His-Ala-Glu-Gly-Thr-Phe-Thr-Ser-Asp-Val-Ser-Ser-Tyr-OCam-Leu-OH (SEQ ID NO: 9) and the 18-mer peptide nucleophile H-Leu-Glu-Gly-Gln-Ala-Ala-Lys-Glu-Phe-Ile-Ala-Trp-Leu-Val-Arg-Gly-Arg-Gly (SEQ ID NO: 10), in the presence of a Subtilisin BPN' variant. Although it was expected that the presence of the hydrophobic amino acid residue, Val, at the P4 position of the C-terminal ester would make these fragments particularly good fragments to make the Liraglutide amino acid sequence at a high yield, this peptide was obtained in a very low yield (see Example 1). As illustrated by Example 2, the yield by enzymatic preparation of H-Liraglutide-1-31-OH from the corresponding 9-mer C-terminal ester and 22-mer peptide nucleophile was even less although it was expected that the presence of a hydrophobic Phe residue on the P4 position would make these fragments particularly good fragments for an enzymatic condensation reaction.

SUMMARY OF THE INVENTION

It is an object of the present invention to provide a novel method of enzymatically synthesizing GLP-1 or an analogue thereof, in particular Liraglutide or Semaglutide. There is a need for alternative enzymatic peptide synthesis processes for these peptides in general, in particular in order to broaden the palette of tools for making them. In particular it is an object to provide such a process that overcomes one or more of the problems mentioned above or discussed in the above cited prior art, more in particular an improved overall yield or an improved selectivity.

One or more other objects that may be subject of the invention follow from the description below.

It has now surprisingly been found that one or more of these objects are met by a method wherein GLP-1 or an analogue thereof is prepared in a method comprising the enzymatic synthesis of a peptide by fragment condensation, wherein two specific fragments of said peptide are coupled in the presence of a ligase, in particular a subtilisin variant or homologue.

Accordingly, the present invention relates to a method for synthesising a peptide comprising the sequence His-X-Glu-Gly-Thr-Phe-Thr-Ser-Asp-Val-Ser-Ser-Tyr-Leu-Glu-Gly-Gln-Ala-Ala-Y-Glu-Phe-Ile-Ala-Trp-Leu-Val-Z-Gly-Arg-Gly (SEQ ID NO: 4), wherein X is Ala or an α-amino-isobutyric acid residue (Aib);

Y is Lys, which Lys has a free side-chain ε-amino group (i.e. a non-derivatised lysine residue), or of which the side-chain ε-amino group is protected with a protective group, or which is functionalized with an amino acid or another functional group;

Z is Arg or Lys;

the method comprising enzymatically coupling
(a) a peptide C-terminal ester or thioester comprising a first peptide fragment comprising the sequence His-X-Glu-Gly-Thr-Phe-Thr-Ser-Asp-Val-Ser-(thio)ester (SEQ ID NO: 11), and
(b) a peptide nucleophile having an N-terminally unprotected amine comprising a second peptide fragment comprising the sequence H-Ser-Tyr-Leu-Glu-Gly-Gln-Ala-Ala-Y-Glu-Phe-Ile-Ala-Trp-Leu-Val-Z-Gly-Arg-Gly (SEQ ID NO: 12);

which enzymatic coupling is catalyzed by a ligase.

It is in particular surprising that a method according to the invention allows the synthesis of the peptide of interest (the ligation product) in a high yield, also when carried out in an aqueous reaction medium. After all, the Ser at the P4 position of the C-terminal (thio)ester fragment is polar, which from a scientific perspective was expected to be unfavourable for the enzymatic coupling reaction.

This has been accomplished without needing any side-chain protective groups on the peptide fragments, and without needing one or both of the fragments to be provided with a functional group to increase solubility (e.g. a 2-hydroxy-4-methoxybenzyl amide group on the peptide backbone amide functionality or a peptide-tag of polar amino acids at the terminal ends of the respective fragments not taking part in the coupling reaction), although in a specific embodiment use may be made of protective groups or solubility-enhancing groups. The high S/H ratio without needing a solubility-enhancing group is surprising because the solubility of the peptide nucleophile is low.

In a method according to the invention, the Y of the peptide nucleophile can be a Lys having a free side-chain ε-amino group (i.e. a non-derivatised lysine residue). However, the invention also allows the coupling of a peptide nucleophile wherein Y is a Lys of which the side-chain ε-amino group comprises a functional group, in particular wherein Y is Lys(γ-Glu), Lys(AEEA-AEEA-γ-Glu, Lys(Pal-γ-Glu-OH) or Lys(AEEA-AEEA-γ-Glu-17-carboxyheptadecanoyl-OH). It is in particular surprising that efficient enzymatic coupling is also possible using such peptide nucleophiles, despite the presence of such groups that are sterically very demanding. In this respect it is further surprising that a high synthesis over hydrolysis ratio (S/H-ratio) is achieved also in an aqueous reaction medium while the peptide nucleophile has a high hydrophobicity, which is increased by the presence of a hydrophobic group (such as a fatty acid tail) at the side-chain ε-amino group of the Lys. Generally, it is the inventors finding that the S/H ratio is directly related to the concentration of the nucleophile and thus to the solubility of the nucleophile in aqueous solution. Since the presence of a hydrophobic functional group renders the solubility of the resulting molecules very low, it is thus very surprising that the S/H ratios are still very high, when coupling the (thio)ester to the peptide nucleophile as defined in the present invention, i.e. comprising the 11-mer peptide (thio)ester and the 20-mer peptide nucleophile. Reference methods wherein it was attempted to obtain the same ligation product by coupling a different (thio)ester and peptide nucleophile provided with or without the side-chain functionality at the Y position, e.g. the corresponding 9-mer (thio)ester and 22-mer peptide nucleophile were not successful.

Coupling with a peptide nucleophile wherein Y is a Lys of which the side-chain ε-amino group has been functionalized with an amino acid or another functional group has in particular been found possible with subtilisin BPN' variants, as described in further detail elsewhere herein. Preferred embodiments of methods wherein the coupling is carried out using a peptide nucleophile wherein Y is a Lys of which the side-chain ε-amino group is functionalized will also be described in further detail below.

DETAILED DESCRIPTION OF THE INVENTION

For the purpose of this invention, with "synthesis over hydrolysis ratio" (S/H ratio) is meant the amount of enzymatically synthesized (oligo)peptide product divided by the amount of (oligo)peptide C-terminal ester or thioester of which the ester or thioester group has been hydrolysed. For further details on determining an S/H ratio, reference is made to WO 2016/056913.

The term "or" as used herein is defined as "and/or" unless it is specified otherwise or it follows from the context that it means "either . . . or . . . ".

The term "a" or "an" as used herein is defined as "at least one" unless it is specified otherwise or it follows from the context that it should refer to the singular only.

When referring to a noun (e.g. a compound, an additive, etc.) in the singular, the plural is meant to be included, unless it follows from the context that it should refer to the singular only.

The term 'pH' is used herein for the apparent pH, i.e. the pH as measured with a standard, calibrated pH electrode.

For the purpose of this invention, with "peptides" is meant any chain composed of two or more amino adds. Thus, peptides are generally amides at least conceptually composed of two or more amino carboxylic acid molecules (i.e. amino adds) by formation of a covalent bond from the carbonyl carbon of one to the nitrogen atom of another with formal loss of water. The term 'peptide' is usually applied to structures formed from α-amino acids, although a peptide may comprise other amino adds, such as one or more beta-amino acids and/or one or more γ-amino adds.

The amino acid sequence of a peptide is referred to as the primary structure. In an embodiment the peptide is essentially free of a secondary structure and essentially free of a tertiary structure.

In an embodiment a peptide that has been synthesized or that is to be coupled in a method according to the invention essentially consists of amino acid residues. E.g. GLP-1 consists of amino add residues. In a further embodiment the peptide essentially consists of amino acid units and protective groups.

In a further embodiment a peptide that has been synthesized or that is to be coupled in a method according to the invention is a conjugate of a peptide chain and another residue, such as a fatty acid. These peptides are called lipopeptides. Fatty acids can e.g. be used to change the solubility. Examples of suitable fatty acids, are C8-C24 saturated fatty acids and C8-C24 unsaturated fatty adds. If desired, a polar linker is provided between the peptide and the fatty acid, e.g. to increase the solubility in an aqueous environment. Liraglutide and Semaglutide are peptides that are conjugates of a peptide chain and a fatty add. Semaglutide comprises a polar linker between the peptide and the fatty acid residue.

Typically, peptides—which term includes oligopeptides, proteins and chimeric peptides—comprise up to about 35 000 amino acid units, in particular 3-20 000, more in particular 4-1000 or 5-500 amino acid units. The ligase according to the invention may be used for the synthesis of other peptides than His-X-Glu-Gly-Thr-Phe-Thr-Ser-Asp-Val-Ser-Ser-Tyr-Leu-Glu-Gly-Gln-Ala-Ala-Y-Glu-Phe-Ile-Ala-Trp-Leu-Val-Z-Gly-Arg-Gly (SEQ ID NOS: 4-7). Such peptides preferably comprise 500 amino acid units or less, in particular 200 or less, more in particular 100 or less. In a specifically preferred embodiment the synthesized peptide comprises at least 10 amino acid units, more specifically at least 15 amino acids, at least 25 amino acids or at least 40 amino acids. The fragments from which such peptide can be chosen within wide ranges; the length of a fragment can be at least 2, in particular at least 5, more in particular at least 10, with the upper limit determined by the length of the synthesized peptide.

With "oligopeptides" is meant within the context of the invention, a peptide composed of 2-200 amino acid units, in particular composed of 5-100 amino acid units, more in particular composed of 10-50 amino acid units.

For the purpose of this invention, with "peptide bond" is meant the amide bond between (i) either the α-amino terminus of one α-amino acid or the beta-amino terminus of one beta-amino acid and (ii) either the α-carboxyl terminus of one other α-amino acid or the beta-carboxyl terminus of one other beta-amino acid. Preferably, the peptide bond is between the α-amino terminus of one α-amino acid and the α-carboxyl terminus of another α-amino acid.

In the context of the invention with "amino acid sidechain" is meant any proteinogenic or non-proteinogenic amino acid side-chain.

Proteinogenic amino adds are the amino acids that are encoded by the genetic code. Proteinogenic amino acids include: alanine (Ala), valine (Val), leucine (Leu), isoleucine (lie), serine (Ser), threonine (Thr), methionine (Met), cysteine (Cys), asparagine (Asn), glutamine (Gin), tyrosine (Tyr), tryptophan (Trp), glycine (Gly), aspartic acid (Asp), glutamic acid (Glu), histidine (His), lysine (Lys), arginine (Arg), proline (Pro) and phenylalanine (Phe). Selenocysteine (Sec, U) is an amino acid, whose structure corresponds to cysteine, with the proviso that it contains a selenium instead of a sulphur atom. Proteinogenic amino adds are the L-stereoisomers of said amino acids (except for glycine, which does not have a stereo-isomeric form).

The non-proteinogenic amino acid of particular interest in a method according to the present invention is 2-aminoisobutyric acid (Aib), which forms part of the peptide chain of Semaglutide.

The term "(thio)ester" is used herein as short-hand for the phrase "ester or thioester".

The term "N-terminal protection" is used herein to indicate that an N-terminal amine group of a peptide, typically the N-terminal α-amine group, is provided with a protective group, generally at least substantially protecting the N-terminal amine group from being coupled to a C-terminal carboxylic group of another peptide or of the same peptide molecule.

The term "C-terminal protection" is used herein to indicate that a C-terminal carboxylic group of a peptide, typically the C-terminal α-carboxylic group is provided with a protective group, generally substantially protecting the carboxylic group from being coupled to an N-terminal amine group of another peptide or of the same peptide molecule.

The term 'mutated' or "mutation" as used herein regarding proteins or polypeptides—in particular enzymes such as ligases—means that at least one amino acid in the wild-type or naturally occurring protein or polypeptide sequence has been replaced with a different amino acid, inserted into, appended to, or deleted from the sequence via mutagenesis of nucleic acids encoding these amino acids. Mutagenesis is a well-known method in the art, and includes, for example, site-directed mutagenesis by means of PCR or via oligonucleotide-mediated mutagenesis as described in Sam brook et al., Molecular Cloning-A Laboratory Manual, 2nd ed., Vol. 1-3 (1989). The term 'mutated' or 'mutation' as used herein regarding genes means that at least one nucleotide in the nucleic acid sequence of that gene or a regulatory sequence thereof, has been replaced with a different nucleotide, has been inserted into, has been appended to, or has been deleted from the sequence via mutagenesis, resulting in the transcription of a protein sequence with a qualitatively of quantitatively altered function or resulting in the knock-out of that gene.

In the present specification, a shorthand for denoting amino acid substitutions employs the single letter amino acid code of the amino acid that is substituted, followed by the number designating where in the protein amino acid sequence the substitution is made. This number is the amino acid position of the wild-type amino acid sequence. Thus for the mutated amino acid sequence it is the amino acid position corresponding to the position with that number in the wild type enzyme. Due to one or more other mutations at a lower position (additions, insertions, deletions, etc.) the actual position does not need to be the same. The skilled person will be able to determine the corresponding positions using a generally known alignment technique, such as NEEDLE. The number is followed by the single letter code of the amino acid that replaces the wild-type amino acid therein. For example, S221C denotes the substitution of serine at the position corresponding to position 221 to cysteine. X is used to indicate any other proteinogenic amino acid than the amino acid to be substituted. For example, S221X denotes the substitution of serine at the position corresponding to position 221 to any other proteinogenic amino acid.

The term "ligase" is used herein for an enzyme having catalytic activity in the coupling of two peptides by catalysing the formation of a peptide bond by coupling the C-terminus of a first peptide and the N-terminus of another peptide. Generally, the ligase (used in a method) according to the invention has ligase activity with respect to coupling an 11-mer His-X-Glu-Gly-Thr-Phe-Thr-Ser-Asp-Val-Ser-(thio)ester (SEQ ID NO: 11), and a 20-mer peptide nucleophile H-Ser-Tyr-Leu-Glu-Gly-Gln-Ala-Ala-Y-Glu-Phe-Ile-Ala-Trp-Leu-Val-Z-Gly-Arg-Gly (SEQ ID NO: 12).

As defined by Schechter and Berger, the active site residues in proteases, including ligases are composed of contiguous pockets termed subsites. Each subsite pocket binds to a corresponding residue in the peptide substrate sequence, referred to here as the sequence position. According to this definition, amino add residues in the substrate sequence are consecutively numbered outward from the cleavage sites as. —P4-P3-P2-P1-P1'-P2'-P3'-P4'-. (the sdssile bond is located between the P1 and PT positions), while the subsites (pockets) in the active site are correspondingly labelled as. —S4-S3-S2-S1-S1'-S2'-S3'-S4'-. (Schechter and Berger, Biochem Biophys Res Commun. 1967 Apr. 20; 27(2):157-62)). It should be noted that not all proteases have all of said subsites. E.g. an S3' and/or an S4' pocket may be absent in a subtilisin BPN' variant or homologue thereof according to the invention.

For the purpose of this invention, with "S1, S2, S3 and S4 pocket" is meant the amino adds of a protease (in particular a ligase) which interact with the amino adds of a peptide acyl donor. The C-terminal amino acid ($1^{st}$ amino acid; P1) of the acyl donor peptide interacts with the amino adds in the S1 pocket of the protease. The penultimate amino acid ($2^{nd}$ amino acid from the C-terminal end; P2) of the acyl donor peptide interacts with the amino adds in the S2 pocket of the protease, the third amino acid (P3) with the S3 and the fourth amino acid (P4) with the S4 pocket. The S1-S4 binding pockets of a protease are defined by several amino acids which can be distant in the primary structure of the protease, but are close in the three dimensional space. For the purpose of this invention, with S1' and S2' pockets are meant the amino adds of a protease which interact with the N-terminal amino adds of a peptide nucleophile. The N-terminal amino add of the peptide nucleophile interacts with the amino adds in the ST pocket of the protease. The N-terminal penultimate amino acid of the peptide nucleophile interacts with the amino acids in the S2' pocket of the protease. The S1' and S2' binding pockets of a protease are defined by several amino acids which can be distant in the primary structure of the protease, but are close in the three dimensional space.

When an enzyme is mentioned with reference to an enzyme class (EC) between brackets, the enzyme class is a class wherein the enzyme is classified or may be classified, on the basis of the Enzyme Nomenclature provided by the Nomenclature Committee of the International Union of Biochemistry and Molecular Biology (NC-IUBMB), which nomenclature may be found at http://www.chem.qmul.ac.uk/iubmb/enzyme/. Other suitable enzymes that have not (yet) been classified in a specified class but may be classified as such, are meant to be included.

Homologues typically have an intended function in common with the peptide or enzyme, of which it is a homologue, such as being capable of catalyzing the same reaction, in particular an enzymatic coupling of a method according to the invention.

Amino acid or nucleotide sequences are said to be homologous when exhibiting a certain level of similarity. Whether two homologous sequences are closely related or more distantly related is indicated by "percent identity" or "percent similarity", which is high or low respectively.

The terms "homology", "percent homology", "percent identity" or "percent similarity" are used interchangeably herein. For the purpose of this invention, it is defined here that in order to determine the percent identity of two amino acid sequences, the complete sequences are aligned for optimal comparison purposes. In order to optimise the alignment between the two sequences gaps may be introduced in any of the two sequences that are compared. Such alignment is carried out over the full length of the sequences being compared. Alternatively, the alignment may be carried out over a shorter length, for example over about 20, about 50, about 100 or more nucleic acids or amino adds. The percentage identity is the percentage of identical matches between the two sequences over the reported aligned region.

A comparison of sequences and determination of percent identity between two sequences can be accomplished using a mathematical algorithm. The skilled person will be aware of the fact that several different computer programs are available to align two sequences and determine the homology between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent identity between two amino acid sequences can be determined using the Needleman and Wunsch algorithm for the alignment of two sequences. (Needleman, S. B. and Wunsch, C. D. (1970) J. Mol. Biol. 48, pp 443-453). The Needleman-Wunsch algorithm has been implemented in the computer program NEEDLE. For the purpose of this invention the NEEDLE program from the EMBOSS package was used (version 2.8.0 or higher, *EMBOSS: The European Molecular Biology Open Software Suite* (2000) Rice, P. Longden, I. and Bleasby, A. Trends in Genetics 16, (6) pp 276-277, http://emboss.bioinformatics.nl/). For protein sequences, EBLOSUM62 is used for the substitution matrix. Other matrices can be specified. The optional parameters used for alignment of amino acid sequences are a gap-open penalty of 10 and a gap extension penalty of 0.5. The skilled person will appreciate that all these different parameters will yield slightly different results but that the overall percentage identity of two sequences is not significantly altered when using different algorithms.

The homology or identity between the two aligned sequences is calculated as follows: the number of corresponding positions in the alignment showing an identical amino acid in both sequences divided by the total length of the alignment after subtraction of the total number of gaps in the alignment. The identity defined as herein can be obtained from NEEDLE by using the NOBRIEF option and is labelled in the output of the program as "longest-identity". For purposes of the invention the level of identity (homology) between two sequences is calculated according to the definition of "longest-identity" as can be carried out by using the program NEEDLE.

The polypeptide sequences, in particular enzyme sequences, can further be used as a "query sequence" to perform a search against sequence databases, for example to identify other family members or related sequences. Such searches can be performed using the BLAST programs. Software for performing BLAST analyses is publicly available through the National Center for Biotechnology Information (http://www.ncbi.nlm.nih.gov). BLASTP is used for amino acid sequences. The BLAST program uses as defaults:

Cost to open gap: default=11 for proteins
Cost to extend gap: default=1 for proteins
Expect value: default=10
Wordsize: default=28 for megablast/3 for proteins Furthermore the degree of local identity (homology) between the amino acid sequence query and the retrieved homologous sequences is determined by the BLAST program. However only those sequence segments are compared that give a match above a certain threshold. Accordingly the program calculates the identity only for these matching segments. Therefore the identity calculated in this way is referred to as local identity.

The term "homologue" is used herein in particular for peptides, more in particular enzymes, having a sequence identity of at least 50%, preferably at least 60%, more preferably at least 70%, at least 80%, at least 90%, at least 95%, at least 96%, at least 97%, at least 98% or at least 99% with the peptide, in particular enzyme, with which the homologue peptide or enzyme is compared. Evidently, the sequence identity will be less than 100%. The percentage of sequence identity will depend on the number of mutations and the length of the peptide (enzyme) with which the homologue is compared. In 'longest identity' alignment deletions are not taken into account.

For the purpose of this invention, with "condensation" is meant the formation of a new amide bond between the C-terminal carboxylic function of a peptide) with the N-terminal amine function of a nucleophile, in particular another peptide.

The term "analogue" of a peptide is used in particular for peptides that are structural analogues and/or functional analogues of said peptide. Functional analogues have a same in vivo target (e.g. the same target receptor on a ceil membrane); structural analogues have a high similarity in amino acid sequence. Functional analogues of a peptide may have a relatively low amino acid sequence identity, e.g. of about 50% or less over the full amino acid sequence, yet a high sequence identity (and thus a high structural similarity) with the peptide of which they are an analogue in a segment of the amino acid sequence, such as near the N-terminal part or near the C-terminal part A structural analogue, in particular comprises an amino add sequence that has at least 60%, more in particular at least 70%, preferably at least 80%, more preferably at least 90% sequence identity, more preferably at least 95% sequence identity with the amino acid sequence of the peptide of which a peptide is an analogue. For the purpose of clarity and a concise description features are described herein as part of the same or separate embodiments, however, it will be appreciated that the scope of the invention may include embodiments having combinations of all or some of the features described. Terms used herein that are not specifically defined herein are as defined in WO 2016/056913, or—if not defined therein—used in accordance with common general knowledge.

The peptide C-terminal ester or thioester comprises a first peptide fragment comprising the amino acid sequence His-X-Glu-Gly-Thr-Phe-Thr-Ser-Asp-Val-Ser-(thio)ester (SEQ ID NO: 11), wherein X is Ala or an α-amino-isobutyric acid unit (Aib). Particularly good results have been achieved with a first peptide fragment wherein this is the amino acid sequence of the first peptide fragment. In a specific embodiment the N-terminal end is extended with at least one amino acid ($W_v$, see below), e.g. Gly or Phe, and the N-terminal end of the extended peptide is provided with a protective group, typically an Edman-type protective group (see also below). If desired, the N-terminal end can be provided with a peptide tag, e.g. to modify solubility in the reaction medium. However, this is generally not required, especially not in an aqueous reaction medium.

The peptide C-terminal ester or thioester typically is an activated (thio)ester, i.e. it contains a carboxy ester or carboxy thioester group that can take part in the enzymatic coupling reaction. In principle, any (substituted or unsubstituted) alkyl or (substituted or unsubstituted) aryl (thio) ester can be used. Typical examples of (thio)esters which can take part in the enzymatic coupling reaction are methyl-, ethyl-, propyl-, isopropyl-, phenyl-, benzyl- (such as p-carboxy-benzyl-), 2,2,2-trichloroethyl-, 2,2,2-trifluoroethyl-, cyanomethyl- and carboxyamidomethyl-(thio)esters.

Particularly good results have been obtained with carboxyamidomethyl-type esters (Gam-esters) represented by the formula peptide-(C=O)—O—$CX_1X_2$—C(=O)N—$R_1R_2$. Herein, each $X_1$ and $X_2$ independently represents a hydrogen atom or an alkyl group. Good results have been achieved when both $X_1$ and $X_2$ are a hydrogen atom (peptide-(C=O)—O—$CH_2$—C(=O)N—$R_1R_2$). Herein $R_1$ represents a hydrogen atom or an alkyl group and $R_2$ represents a hydrogen atom or an alkyl group or an amino acid or a peptide residue with a C-terminal carboxyamide or carboxylic acid functionality, optionally protected on the side-chain functionality of the amino acid or on one or more of the side-chain functionalities of the amino acids. Herein, each alkyl group may independently represent a (substituted or unsubstituted) C1-C7 alkyl group, preferably a (substituted or unsubstituted) linear C1-C6 alkyl group, more preferably a (substituted or unsubstituted) linear C1-C3 alkyl group, and most preferably a methyl group. Good results have in particular been achieved in a method of the invention wherein both $R_1$ and $R_2$ represent a hydrogen atom or wherein $R_1$ represents a hydrogen atom and $R_2$ represents an amino acid or peptide residue with a C-terminal carboxyamide or carboxylic acid functionality, optionally protected on the side-chain functionality of the amino acid or on one or more of the side-chain functionalities of the amino adds.

It is especially advantageous to use a Cam-AA1-AA2-ester, wherein AA1 is a first amino acid residue and AA2 is a second amino acid residue. Herein AA1 is a hydrophobic amino acid residue, such as an alanine, valine, leucine, isoleucine, phenylalanine, methionine or tryptophan unit AA2 is a basic amino add residue, such as an arginine or a lysine unit. Particularly preferred are Cam-Phe-Arg and Cam-Phe-Lys. The AA1 and the AA2 typically have a free side-chain functionality, i.e. that is free of a protective group or another residue.

Particularly good results have also been obtained with carboxyl substituted benzyl esters, in particular with p-carboxyl substituted benzyl esters represented by the formula peptide-(C=O)—O—$CH_2$—$C_6H_4$—$CO_2E$ wherein E represents a hydrogen atom, a positively charged salt ion such as an ammonium ion, or an amino acid or a peptide residue with a C-terminal carboxyamide or carboxylic acid functionality, optionally protected on the side-chain functionality of the amino acid or on one or more of the side-chain functionalities of the amino adds. Good results have also been obtained with p-carboxyl substituted benzyl esters represented by the formula peptide-(C=O)—O—$CH_2$—$C_6H_4$—$CO_2E$ wherein E is defined as above and in which one or more hydrogen atoms in the phenyl ring ($C_6H_4$ in the above formula) are replaced by a substituent such as hydroxy, alkoxy, aryloxy or halogen.

The peptide C-terminal (thio)ester can be N-terminally unprotected or N-terminally protected.

Suitable N-terminal protecting groups are those N-protecting groups which can be used for the synthesis of peptides. Such groups are known to the person skilled in the art Examples of suitable N-protecting groups include carbamate or acyl type protecting groups, for instance 'Cbz' (benzyloxycarbonyl), 'Boc' (tert-butytoxycarbonyl), 'For' (formyl), 'Fmoc' (9-fluorenylmethoxycarbonyl), 'PhAc' (phenacetyl) and 'Ac' (acetyl). The groups For, PhAc and Ac may be introduced and cleaved enzymatically using the enzymes Peptide Deformylase, PenG acylase or Acylase, respectively.

The inventors further realized that a substituted thiocarbamoyl group, such as a phenylthiocarbamoyl (PTC) group is a useful protective group for the N-terminal α-amine function of the C-terminal (thio)ester in a method for enzymatically synthesizing peptides by fragment condensation. The use of such groups as such is e.g. well known from Edman degradation processes. Protective agents that can be used for Edman-type amino acid sequencing are also referred to herein as Edman-type protective agents, and likewise agents coupled to an amine group (in particular the N-terminal amine) of a peptide are referred to herein as Edman-type protective groups. The inventors found that an Edman-type protective agent—attached to the N-terminal α-amino function via a linking additional amino acid, e.g. glycine—forms an effective protecting group, when after the enzymatic coupling reaction the obtained peptide needs to be provided with a functional group at position Y to obtain Liraglutide or Semaglutide, e.g. when coupling Pal to the Lys-γ-Glu (Y) or when coupling 17-carboxyheptadecanoic acid to the Lys-AEEA-AEEA-γ-Glu (Y). Substituted thiocarbamoyl groups can be provided to the N-terminal α-amino function by reacting said amine function with the corresponding isothiocyanate under (slightly) alkaline conditions. Hence, a phenylthiocarbamoyl (PTC) group can be introduced using phenylisothiocyanate (PITC) and a methylthiocarbamoyl (MTC) group can be introduced using methylisothiocyanate (MITC). Under acidic conditions such substituted thiocarbamoyl groups are cleaved from the peptide together with the α-amino add to which they are attached in the form of a thiazolinone derivative.

This new way of providing N-terminal protection has been found advantageous over, e.g., Fmoc with respect to solubility in an aqueous reaction system. It has been found advantageous over, e.g. Boc, in terms of compatibility when using solid-phase synthesis. An Edman-type protective group, such as a substituted thiocarbamoyl moiety, functions particularly well as a protective group at neutral or alkaline pH and can be easily removed at acidic pH. Thus, such group is usually employed in a coupling reaction at neutral or alkaline pH, using a ligase having a good S/H ratio at such pH, like a Subtilisin BPN' variant or homologue, as described in more detail elsewhere herein.

Suitable protection/deprotection conditions when using Edman-type protective moieties include those that are generally known in the art for using such moiety in Edman-type degradation methods. A substituted thiocarbamoyl group has been found particularly effective, in combination with contributing to good solubility, also in an aqueous reaction medium. The substituted thiocarbamoyl group can be aromatic or aliphatic. Preferably, the substituted thiocarbamoyl group is an aryl-substituted thiocarbamoyl group, or an alkyl-substituted thiocarbamoyl group. Particularly preferred aryl-substituted thiocarbamoyl groups are C6-C12-aryl-substituted thiocarbamoyl groups, more in particular phenylthiocarbamoyl (PTC). Particularly preferred alkyl-substituted thiocarbamoyl groups are C1-C6-alkyl-substituted thiocarbamoyl groups, more in particular methylthiocarbamoyl (MTC). Further examples of preferred isothiocyanates to be used for the introduction of substituted thiocarbamoyl groups are those mentioned in H. Matsunaga, T. Santa, K. Hagiwara, H. Homma, K. Imai, S. Uzu, K. Nakashima, S. Akiyama, Anal. Chem. 1995, 67, 4276, such as FITC, BAMPITC, DNTC, DNSAPITC, dansylamino-PITC, 3-POPICs, 4-POPICs, CIPIC and 7-[(N,N-dimethylamino)sulphonyl]-2,1,3-benzoxadiazol-4-yl isothiocyanate (DBD-NCS), see the paragraph bridging the left-hand and right hand column of page 4276, incorporated by reference. Yet another preferred example is 7-aminosulphonyl-4-(2,1,3-benzoxadiazolyl)-isothiocyanate (ABD-NCS).

As an alternative to a substituted thiocarbamoyl moiety, another moiety suitable for sequencing amino adds in a peptide with an Edman-type degradation method can be used as a protective group in a similar fashion, i.e. by labeling the N-terminal end of the peptide C-terminal ester with said moiety via a linking amino acid and, after enzymatic coupling with the peptide nucleophile—cleaving the moiety together with the linking amino acid residue from the remainder of the coupling product. Suitable protective moieties that can be labelled to the N-terminal end of a peptide via a linking amino acid residue and cleaved off together with the linking amino acid residue are therefore also referred to herein as 'Edman-type protective groups'.

Further, it is possible to link an Edman-type protective group to the peptide C-terminal (thio)ester via more than one amino acid (i.e. via a peptide chain). The linking amino acids can then be removed by a number of cycles of labeling with the moiety and cleaving off the moiety plus amino acid, in a similar way as is done in a peptide sequencing method. The use of additional linking-amino acids is not necessary, but they can be used—if desired—e.g. to modify the solubility of the peptide C-terminal (thio)ester in a reaction medium of choice.

Thus, in a specific preferred embodiment a method according to the invention comprises enzymatically coupling (a) a peptide C-terminal ester or thioester represented by the formula P—W$_v$-His-X-Glu-Gly-Thr-Phe-Thr-Ser-Asp-Val-Ser-(thio)ester (SEQ ID NO: 11) with (b) the peptide nucleophile. Herein P represents the Edman-type protective group, preferably a phenylthiocarbamoyl (PTC) or a methylthiocarbamoyl (MTC) moiety. Herein, v is an integer of at least 1, usually of 1-10, preferably 1-4, more preferably 1, 2 or 3, most preferably 1 and v represents the number of amino acid residues W. Each W can be the same or different. Usually each W is selected from the group of proteinogenic amino acids, although in principle another amino add could be used, provided it can be cleaved off as a P—W under Edman-type cleaving conditions.

This N-terminally protected peptide C-terminal (thio) ester is coupled with the nucleophile (b), whereby the N-terminally protected peptide P—W$_v$-His-X-Glu-Gly-Thr-Phe-Thr-Ser-Asp-Val-Ser-Ser-Tyr-Leu-Glu-Gly-Gln-Ala-Ala-Y-Glu-Phe-Ile-Ala-Trp-Leu-Val-Z-Gly-Arg-Gly (SEQ ID NOS: 4-7) is formed. Thereafter, this peptide is subjected to a cleavage reaction wherein the peptide W$_{v-1}$-His-X-Glu-Gly-Thr-Phe-Thr-Ser-Asp-Val-Ser-Ser-Tyr-Leu-Glu-Gly-an-Ala-Ala-Y-Glu-Phe-Ile-Ala-Trp-Leu-Val-Z-Gly-Arg-Gly (SEQ ID NOS: 4-7) (which peptide may be elongated at the C-terminus) is formed. If v−1>0, a group P is coupled to the N-terminal α-amino function of W of the peptide, after which P—W is removed by cleavage. A coupling and cleaving cycle is then repeated till the peptide $^1$His-X-Glu-Gly-Thr-Phe-Thr-Ser-Asp-Val-Ser-Ser-Tyr-Leu-Glu-Gly-Gln-Ala-Ala-Y-Glu-Phe-Ile-Ala-Trp-Leu-Val-Z-Gly-Arg-Gly (SEQ ID NOS: 4) is obtained.

Labelling of P to the N-terminal end of the peptide is accomplished in a manner known per se, based on the Edman type methodology known for said P, typically at mildly alkaline conditions, e.g. about pH 8. Cleavage of P—W from the N-terminal end of the peptide is accomplished in a manner known per se, based on the Edman type methodology known for said P, typically at acidic conditions, usually at a pH of about 4 or less, in particular in the range of about 3 or less, e.g. of 0-2. For instance trifluoroacetic acid (TFA) may be used.

N-terminal protection of the peptide (thio)ester is in particular useful in a method wherein Y comprises a Lys(γ-Glu-OH) moiety bearing a free α-amino function which needs to be coupled to palmitic add or if Y comprises a Lys(AEEA-AEEA-γ-Glu-OH) moiety bearing a free α-amino function which needs to be coupled to 17-carboxyheptadecanoic acid.

In particular, good results have been achieved with a peptide C-terminal (thio)ester without protected side-chain functionalities. However, in an embodiment one or more side-chain functionalities, e.g. all side-chain functionalities, are provided with a protecting group. Suitable protecting groups are known to the person skilled in the art. Carboxylic acid groups can for instance be protected with a cyclohexyl, benzyl or allyl group.

The activated C-terminal (thio)ester group of the peptide C-terminal (thio)ester can be synthesized using solid phase synthesis in high yield and purity without racemization. An additional advantage of the use of (thio)esters of the carboxyamidomethyl type wherein $R_1$ represents a hydrogen atom and $R_2$ represents an amino acid or peptide residue with a C-terminal carboxylic acid functionality, optionally protected on the side-chain functionality of the amino acid or on one or more of the side-chain functionalities of the amino adds is, that their activated C-terminal ester or thioester group can be synthesized using the cheap and industrially available 2-chlorotritylchloride resin.

The activated C-terminal (thio)ester group of the peptide C-terminal (thio)ester can also be synthesized by solution phase synthesis or by fermentation, i.e. using a microorganism. As generally known in the art fermentative processes include production of a compound, i.e. a peptide under aerobic or anaerobic conditions. A reliable method to obtain peptide (thio)esters using fermentation is via so-called intein expression (see for instance E. K. Lee, Journal of Chemical Technology and Biotechnology, 2010, 9, 11-18). Different intein expression system kits are commercially available (for instance the IMPACT™ kit). Other methods for the fermentative production of peptide (thio)esters are known in the art.

The peptide nucleophile having an N-terminally unprotected amine comprises the amino acid sequence H-Ser-Tyr-Leu-Glu-Gly-Gln-Ala-Ala-Y-Glu-Phe-Ile-Ala-Trp-Leu-Val-Z-Gly-Arg-Gly (SEQ ID NO: 12) ('the second peptide fragment'). Particularly good results have been achieved with a peptide nucleophile, wherein this is the amino acid sequence of the peptide nucleophile. It is in particular an important advantage of the present invention that—also in an aqueous system—the enzymatic coupling works well without needing the C-terminal end to be extended with a peptide tag or another derivative to enhance solubility or reactivity of the peptide nucleophile.

In an embodiment the peptide nucleophile is C-terminal protected. In another embodiment it is free of C-terminal protection.

In particular, good results have been achieved with peptide nucleophiles without protected side-chain functionalities.

In an embodiment one or more side-chain functionalities (in particular one or more hydroxyl, carboxyl or amine groups) of the peptide nucleophile are provided with a protecting group. Suitable protecting groups are known to the person skilled in the art. Carboxylic acid groups can for instance be protected with a cyclohexyl, benzyl or allyl group; amine functionalities can for instance be protected with an allyloxycarbonyl group or a trifluoroacetyl group.

The peptide nucleophile may be synthesized using methods known in the art, such as solid phase synthesis, solution phase synthesis or by fermentation.

As mentioned above, Y is Lys, of which Lys the side-chain ε-amino group may be protected with a protective group. However, it is generally not necessary for a satisfactory coupling yield and rate to protect the side-chain ε-amino group, in particular not if a subtilisin or homologue thereof is used as the ligase. In particular, a subtilisin BPN' variant or homologue as described herein is suitable to couple both fragments also when the ε-amino group of Lys at position Y is free of a protective group.

Accordingly, usually the Y of the peptide nucleophile is a lysine residue having a free ε-amino side chain or having a functionalized ε-amino side chain. The product obtained by the enzymatic coupling can be the peptide of interest (optionally after removal of protective groups, if any), e.g. if GLP-1 is the peptide of interest to be synthesized or if Y of the peptide nucleophile already comprises the needed functionalization to obtain Liraglutide of Semaglutide. Alternatively, the product obtained by enzymatic coupling can subsequently be subjected to further reactions to functionalize it in particular with an amino acid or another functional group, more in particular a functional group selected from the group consisting of Pal-γ-Glu-OH, and AEEA-AEEA-γ-Glu-N-17-carboxyheptadecanoyl-OH, wherein Pal is palmitoyl and AEEA-AEEA is 2-[2-(2-aminoethoxy)ethoxy]acetyl-2-[2-(2-aminoethoxy)ethoxy]acetyl. Ways to functionalize the free amino add side chain of Y to yield Liraglutide or Semaglutide or to provide the peptide nucleophile suitable for synthesising Liraglutide or Semaglutide can be based on methodology generally known in the art or may be based on the present examples or on the technology described in the literature referred to in the references cited herein. In particular, a functionalization protocol may be used based on U.S. Pat. No. 6,451,974 B1.

In a particularly preferred embodiment the peptide that is synthesized in a method according to the invention is Liraglutide.

The present invention is advantageous in that it allows enzymatically coupling (a) the peptide C-terminal ester or thioester comprising the first peptide fragment said first fragment comprising the sequence His-Ala-Glu-Gly-Thr-Phe-Thr-Ser-Asp-Val-Ser-(thio)ester (SEQ ID NO: 11), and (b) the peptide nucleophile comprising the second peptide fragment said second fragment comprising the sequence H-Ser-Tyr-Leu-Glu-Gly-Gln-Ala-Ala-Y-Glu-Phe-Ile-Ala-Trp-Leu-Val-Arg-Gly-Arg-Gly (SEQ ID NO: 13), wherein Y is Lys(Pal-γ-Glu-OH). Thus, the enzymatic coupling may be carried out coupling the corresponding 11-mer peptide C-terminal (thio)ester and 20-mer N-terminal nucleophile, thereby obtaining Liraglutide. Although the N-terminal α-amino function of the peptide (thio)ester may be provided with a protective group such as a group represented by P—W$_v$, as defined elsewhere herein when describing Edman-type protective groups, particularly good results have inter alia been achieved with a method wherein the peptide nucleophile having Y=Lys(Pal-γ-Glu-OH) is coupled to the peptide C-terminal ester or thioester represented by the formula His-Ala-Glu-Gly-Thr-Phe-Thr-Ser-Asp-Val-Ser-(thio)ester (SEQ ID NO: 11) without any protection of the N-terminal end of the peptide (thio)ester and without needing any further protective groups.

In a further preferred embodiment, Liraglutide is prepared in a method comprising enzymatically coupling (a) the peptide C-terminal ester or thioester comprising the first peptide fragment said first fragment comprising the sequence His-Ala-Glu-Gly-Thr-Phe-Thr-Ser-Asp-Val-Ser-(thio)ester (SEQ ID NO: 11), and (b) the peptide nucleophile comprising the second peptide fragment said second fragment comprising the sequence H-Ser-Tyr-Leu-Glu-Gly-Gln-Ala-Ala-Lys(γ-Glu-OH)-Glu-Phe-Ile-Ala-Trp-Leu-Val-Arg-Gly-Arg-Gly (SEQ ID NO NO: 13); and thereafter providing said Lys (γ-Glu-OH) residue with a palmitoyl group (Pal), thereby obtaining the Liraglutide. In this embodiment the N-terminal α-amino function of the peptide C-terminal ester or thioester is usually protected during enzymatic coupling, preferably with an Edman-type protective group.

In a further particularly preferred embodiment, Liraglutide is prepared by a method comprising enzymatically coupling (a) the peptide C-terminal ester or thioester comprising the first peptide fragment said first fragment comprising the sequence His-Ala-Glu-Gly-Thr-Phe-Thr-Ser-Asp-Val-Ser-(thio)ester (SEQ ID NO: 11), and (b) the peptide nucleophile comprising the second peptide fragment said second fragment comprising the sequence H-Ser-Tyr-Leu-Glu-Gly-Gln-Ala-Ala-Y-Glu-Phe-Ile-Ala-Trp-Leu-Val-Arg-Gly-Arg-Gly (SEQ ID NO: 12-13), wherein Y is a lysine residue having a free ε-amino side chain; and thereafter providing said ε-amino side chain with Pal-γ-Glu-OH, thereby obtaining the Liraglutide. In this embodiment particularly good results have been achieved without using any protective group at the N-terminal α-amino function of the peptide (thio)ester.

In an alternative embodiment a method according to the invention comprises the synthesis of Semaglutide.

In an advantageous embodiment the synthesis of Semaglutide comprises enzymatically coupling (a) the peptide C-terminal ester or thioester comprising the first peptide fragment said first fragment comprising the sequence His- Aib-Glu-Gly-Thr-Phe-Thr-Ser-Asp-Val-Ser-(thio)ester (SEQ ID NO: 11), and (b) the peptide nucleophile comprising the second peptide fragment said second fragment comprising the sequence H-Ser-Tyr-Leu-Glu-Gly-Gln-Ala-Ala-Y-Glu-Phe-Ile-Ala-Trp-Leu-Val-Arg-Gly-Arg-Gly (SEQ ID NO: 12), wherein Y is Lys(AEEA-AEEA-γ-Glu-N-17-carboxyheptadecanoyl-OH). Thereby the Semaglutide can be directly obtained. Although the N-terminal α-amino function of the peptide (thio)ester may be provided with a protective group such as a group represented by P—W$_v$, as defined elsewhere herein when describing Edman-type protective groups, particularly good results have inter alia been achieved with a method wherein the peptide nucleophile with Y=Lys(AEEA-AEEA-γ-Glu-N-17-carboxyheptadecanoyl-OH is coupled to the peptide C-terminal ester or thioester represented by the formula His-Ala-Glu-Gly-Thr-Phe-Thr-Ser-Asp-Val-Ser-(thio)ester (SEQ ID NO: 11) without any protection of the N-terminal α-amino function of the peptide (thio)ester and without needing any further protective groups.

In a further embodiment a method for the synthesis of Semaglutide comprises enzymatically coupling (a) the peptide C-terminal ester or thioester comprising the first peptide fragment said first fragment comprising the sequence His-Aib-Glu-Gly-Thr-Phe-Thr-Ser-Asp-Val-Ser-(thio)ester (SEQ ID NO: 11), and (b) the peptide nucleophile comprising the second peptide fragment said second fragment comprising the sequence H-Ser-Tyr-Leu-Glu-Gly-Gln-Ala-Ala-Y-Glu-Phe-Ile-Ala-Trp-Leu-Val-Arg-Gly-Arg-Gly (SEQ ID NO: 12), wherein Y is Lys(AEEA-AEEA-γ-Glu-OH), and thereafter providing the Lys(AEEA-AEEA-v-Glu-OH) moiety with a 17-carboxyheptadecanoyl group. Thus, Semaglutide can be obtained by further functionalization after enzymatic coupling. In this embodiment the N-terminal α-amino function of the peptide C-terminal ester or thioester is usually protected during enzymatic coupling, preferably with an Edman-type protective group.

In a further embodiment the Semaglutide is obtained by a method comprising enzymatically coupling (a) the peptide C-terminal ester or thioester comprising the first peptide fragment said first fragment comprising the sequence His-Aib-Glu-Gly-Thr-Phe-Thr-Ser-Asp-Val-Ser-(thio)ester, and (b) the peptide nucleophile comprising the second peptide fragment said second fragment comprising the sequence H-Ser-Tyr-Leu-Glu-Gly-Gln-Ala-Ala-Y-Glu-Phe-Ile-Ala-Trp-Leu-Val-Arg-Gly-Arg-Gly (SEQ ID NO: 12), wherein Y is a lysine residue having a free ε-amino side chain, and thereafter providing said ε amino side chain with an AEEA-AEEA-γ-Glu-N-17-carboxyheptadecanoyl-OH group, thereby obtaining the Semaglutide. Thus, Semaglutide can be obtained by functionalization after enzymatic coupling. In this embodiment particularly good results have been achieved without using any protective group at the N-terminal α-amino function of the peptide (thio)ester (or any side-chain functionalities).

In yet another alternative embodiment the peptide that is synthesized is GLP-1.

The ligase used to catalyze the coupling of the peptide C-terminal (thio)ester and the peptide nucleophile can be any ligase having catalytic activity in coupling both peptides by catalysing the formation of a peptide bond between the C-terminus of the peptide C-terminal (thio)ester and the N-terminus of the peptide nucleophile, wherein the S/H ratio for the coupling vs. the hydrolysis of the coupling product in the used reaction medium is larger than 1. Usually, the ligase can be classified as a serine protease which can generally be classified in EC 3.4.21. Generally, it has a catalytic triad in the order Asp, His and Ser.

In particular, a ligase used in a method according to the invention is an isolated enzyme. Thus, it is isolated from the organism wherein it has been expressed, typically a recombinant organism, if it has been produced in an organism, respectively isolated from the reaction medium in which it has been synthesized.

In particular, an enzyme of the invention is considered isolated for the purpose of the invention either in the crude form or substantially purified by any suitable technique such as, for example, the single-step purification method disclosed in Smith and Johnson, Gene 67:31-40 (1988).

In particular, the ligase can be a serine endoprotease. The ligase typically has an S/H ratio larger than 1, preferably 2 or more, in particular 5 or more in the used reaction medium, in particular in a reaction medium comprising water, more in particular an aqueous medium. The upper value of this quotient is not critical; in practice it may e.g. be 100 or less, in particular 20 or less. The ligase used in a method according to the invention generally has an improved "synthesis over hydrolysis ratio" (S/H ratio), at least compared to subtilisin BPN'.

The S/H ratio of the ligases (used in a method) according to the invention divided by the S/H ratio of subtilisin BPN'—at least under the conditions described in the examples—is usually more than 100, preferably 250 or more, more preferably 500 or more, in particular 1000 or more. The upper value of this quotient is not critical; it may approximate infinity.

In particular, very good results have been achieved with a subtilisin BPN' variant or a homologue thereof.

Especially when carrying out the enzymatic coupling in a reaction medium comprising water as a major solvent (e.g. 50-100 wt % based on total liquid) a subtilisin BPN' variant or a homologue thereof according to WO 2016/056913 has been found particularly suitable. The contents of the publication are incorporated by reference, in particular with respect to the details about the subtilisin BPN' variant or a homologue, as present in the claims thereof.

Thus, usually, the ligase used for the coupling reaction is a subtilisin BPN' variant or a homologue thereof comprising the following mutations compared to subtilisin BPN' represented by SEQ ID NO: 2 or a homologue sequence thereof:
  a deletion of the amino acids corresponding to positions 75-83;
  a mutation at the amino acid position corresponding to S221, the mutation being S221C or S221 selenocysteine;
  preferably a mutation at the amino acid position corresponding to P225;
  wherein the amino acid positions are defined according to the sequence of subtilisin BPN' represented by SEQ ID NO: 2.

Further preferred ligases for use in a method according to the invention may comprise one or more additional mutations, in particular one or more further mutations as identified elsewhere herein or in WO 2016/056913, incorporated herein by reference.

The mutation at the amino acid position corresponding to S221 of the ligase, in particular the subtilisin BPN' variant or homologue thereof, preferably is S221C.

The mutation at the amino acid position corresponding to P225 is usually advantageous for the S/H ratio for the enzymatic coupling. The mutation is usually selected from the group of P225N, P225D, P225S, P225C, P225G, P225A, P225T, P225V, P225I, P225L, P225H, P225Q, preferably from the group of P225N, P225D, P225S, P225C and P225G, more preferably P225N or P225D, most preferably P225N.

For a good enzyme stability, the ligase, in particular the subtilisin BPN' variant or homologue thereof, preferably comprises one or more mutations selected from the group of mutations at an amino add position corresponding to Q2, S3, P5, S9, I31, K43, M50, A73, S188, Q206, N212, N218, T254 and Q271 of SEQ ID NO 2.

A preferred mutation at the position corresponding to Q2 corresponds to Q2K.

A preferred mutation at the position corresponding to S3 corresponds to S3C.

A preferred mutation at the position corresponding to P5 corresponds to P5S.

A preferred mutation at the position corresponding to S9 corresponds to S9A.

A preferred mutation at the position corresponding to I31 corresponds to I31L.

A preferred mutation at the position corresponding to K43 corresponds to K43N.

A preferred mutation at the position corresponding to M50 corresponds to M50F.

A preferred mutation at the position corresponding to A73 corresponds to A73L.

A preferred mutation at the position corresponding to S188 corresponds to S188P.

A preferred mutation at the position corresponding to Q206 corresponds to Q206C.

A preferred mutation at the position corresponding to N212 corresponds to N212G.

A preferred mutation at the position corresponding to T254 corresponds to T254A.

A preferred mutation at the position corresponding to 0271 corresponds to Q271E.

In a particularly preferred embodiment the ligase, in particular the subtilisin BPN' variant or homologue thereof, comprises at least six, preferably at least eight more preferably at least 10, in particular 12, 13 or 14 of said mutations selected from the group of mutations at positions corresponding to 02, S3, P5, S9, I31, K43, M50, A73, S188, Q206, N212, T254 and Q271. This is in particular preferred for enzyme stability in a reaction medium comprising water as a major or the only solvent. The ligase may have further mutations compared to subtilisin BPN', provided that it has enzymatic fragment condensation activity (coupling activity) in the preparation of the peptides according to the present invention, in particular one or more further mutations as described in the references cited herein.

Alternatives to subtilisin BPN', as template enzymes from which an enzyme according to the invention, in particular a homologue of a subtilisin BPN' variant of the invention, can be derived by mutagenesis, are other subtilisins, in particular subtilisins having at least 50% homology with subtilisin BPN'.

Sequences of suitable subtilisins can be retrieved from the UNIPROT sequence database (http://www.uniprot.org/), as available on 11 Aug. 2014, by BLASTing the database with subtilisin BPN' (SEQ ID 2) as a query. However, sequence retrieval is not limited to UNIPROT nor to the date. The skilled person in the art knows how to query alternative sequence depositories or to collect additional homologue sequences by sequencing (see for example *Zooming in on metagenomics: molecular microdiversity of Subtilisin Carts- berg in soil*. Gabor E, Niehaus F, Aehle W, Eck J. J Mol Biol. 2012 Apr. 20; 418(1-2): 16-20).

In particular, the invention further relates to variants, having at least said deletions of the amino adds corresponding to L75 till and including G83 of subtilisin BPN', cysteine or selenocystein at a position corresponding to position 221 in subtilisin BPN' and at least one of said further mutations in present claim 1.

The sequence of subtilisin BPN' is given in SEQ ID NO 2 (mature form). The gene encoding for subtilisin BPN' amino acids −107 to 275 is given in SEQ ID NO 1. The subtilisin BPN' variant or homologue can be based on the enzymes according to WO2016/056913, with the proviso that it has the above-mentioned mutations.

In an advantageous embodiment the ligase is a subtilisin BPN' variant having a deletion of the amino acids corresponding to positions 75-83, the mutation S221C and one or more further mutations, preferably at least 3 further mutations, in particular 5-8 further mutations, at amino acid positions corresponding to M222, Y217, P225, F189, N218, E156, G166 and N62 of wild-type subtilisin BPN' (mature).

Of these mutations, in particular good results have been achieved with the mutations corresponding to: M222P, Y217H, P225N, F189W, N218D, E156N, G166E, N62A. SEQ ID NO: 3 shows a subtilisin BPN' variant (for use) according to the invention with deletion of the $Ca^{2+}$ binding loop, S221C and having said further mutations. The His tag was included for facilitating purification and is not needed for ligase activity. Further preferred enzymes may comprise one or more additional mutations, in particular one or more further mutations as identified elsewhere herein or in WO 2016/056913, incorporated herein by reference.

In a method of the invention the enzymatic reaction is typically performed in a fluid comprising water. Preferably the reaction is performed in a buffered fluid. The water content usually is 10-100 vol %, based on total liquids, preferably 20 vol. % or more, preferably 40 vol. % or more, in particular 50 vol. % or more, more in particular 60 vol. % or more. In particular good results have been achieved in a reaction medium, comprising 70-100 vol % water, more in particular 90-100 vol. %, 95-100 vol. % or 98-100 vol. % water. The term 'aqueous' is used for media at least substantially consisting of water.

In principle, any buffer is suitable. Good buffers are known to a person skilled in the art. See for instance David Sheehan in Physical Biochemistry, $2^{nd}$ Ed. Wiley-VCH Verlag GmbH, Weinheim 2009; http://www.sigmaaldrich.com/life-science/core-bioreagents/biological-buffers/tearning-center/buffer-calculator.html. Particularly good results have e.g. been achieved with a Good's buffer, such as tricine. The concentration of the buffer may be chosen within wide limits, e.g. in the range of 10-1000 mM, in particular in the range of 25-500 mM, more in particular in the range of 50-250 mM. A relatively low molarity of the buffer has been found advantageous for coupling a peptide nucleophile wherein Y is Lys(Pal-γ-Glu-OH) or the like.

The pH of the buffer for a coupling reaction in a method according to the invention may be at least 5, in particular at least 6, preferably at least 7. A desired pH is usually less than 11, in particular less than 10, even more preferably less than 9. Usually the optimal pH for the enzymatic coupling is between 7 and 9.

Due to the high S/H ratio, a large excess of the peptide C-terminal ester or thioester or of the peptide nucleophile is generally not needed to reach a high yield in the condensation reaction. Generally, they are contacted in an about stoichiometric ratio or in an excess of the peptide C-terminal ester, in particular in a molar ratio of (a) the peptide C-terminal ester or thioester to (b) the peptide nucleophile in the range of 1:1 to 5:1. Although satisfactory results are achieved with a stoichiometric ratio, an excess of the peptide C-terminal (thio)ester has been found advantageous for the reaction rate. Thus, preferably the molar ratio of (a) the peptide C-terminal ester or thioester to (b) the peptide nucleophile is in the range of 1.05:1.0 to 4:1, more preferably in the range of 1.1:1.0 to 3:1, even more preferably in the range of 1.2:1.0 to 2.5:1.0, in particular in the range of 1.2:1.0 to 2.0:1.0.

In a method of the invention, it may be advantageous to acid additives to the fluid wherein the reaction is carried out to improve the solubility of the peptide fragments or to improve the reaction yield. Such additives may be a salt or an organic molecule, for instance guanidinium hydrochloride, urea, sodium dodecasulphate or Tween. However, good results have been achieved without such additive, also in a fully aqueous reaction medium, e.g. in an embodiment wherein the Y is Lys(Pal-γ-Glu-OH) or the like.

The reaction may be carried out in a fully aqueous liquid or in a mixture of water and a water miscible co-solvent such as N,N-dimethylformamide (DMF), N-methyl-pyrrolidinone (NMP), N,N-dimethylacetamide (DMA), dimethylsulphoxide (DMSO), acetonitrile, an ether, such as tetrahydrofuran (THF), 2-methyl-tetrahydrofuran (Me-THF) or 1,2-dimethoxyethane, or a (halogenated) alcohol, such as methanol, ethanol, isopropanol, tert-butanol, 2,2,2-trifluoroethanol (TFE), 1,1,1,3,3,3-hexafluoroisopropanol, or a mixture of these organic solvents. Depending on the stability of the subtilisin BPN' variant and the solubility of the peptide substrates, the amount of co-solvent is preferably below 70 vol %, more preferably below 60 vol %, even more preferably below 50 vol %, and most preferably below 40%.

In principle the temperature during the enzymatic fragment condensation is not critical, as long as a temperature is chosen at which the ligase to be used shows sufficient activity and stability. Such a temperature can be routinely determined. Generally, the temperature may be at least −10° C., in particular at least 0° C. or at least 10° C. Generally, the temperature may be 70° C. or less, in particular 60° C. or less or 50° C. or less. Optimal temperature conditions can easily be identified for a specific ligase for a specific enzymatic fragment condensation by a person skilled in the art through routine experimentation based on common general knowledge and the information disclosed herein. In general, the temperature advantageously is in the range of 20-50° C.

The invention further relates to the use of an Edman-type agent to provide a protective group in the synthesis of a peptide in a method comprising enzymatic coupling of peptides by fragment condensation. Accordingly, the invention further relates to a method for synthesizing a peptide, comprising enzymatically coupling (a) a peptide C-terminal ester or thioester represented by the formula P—$W_v$-$AA_n$-(thio)ester with a peptide nucleophile represented by the formula $AA_m$, which coupling is catalyzed by a ligase, preferably a subtilisin BPN' variant or homologue, such as described elsewhere herein.

Herein P represents the Edman-type protective group, as defined above, preferably a thiocarbamoyl group. Coupling of P to the N-terminal end of the peptide is accomplished in a manner known per se, based on the Edman type methodology known for said P, typically at mildly alkaline conditions, e.g. about pH 8. Herein v is an integer of at least 1, usually preferably 1-10, preferably 1-5, more preferably 1, 2 or 3, most preferably 1 and v representing the number of amino acid residues W, wherein each W can be the same or different and preferably is as defined as above. Each AA stands for an amino acid residue, n is an integer representing the number of amino acid residues of the peptide C-terminal ester or thioester, and m is an integer representing the number of amino acid residues of the peptide nucleophile. Typically, the sum of n and v is at least 4 in order to allow recognition by the ligase. Preferably, n is in the range of 3-200, in particular in the range of 3-50, more in particular in the range of 3-25. In a specific embodiment n is at least 4, at least 6, at least 8, at least 10, at least 15 or at least 20. Preferably, m is in the range of 3-200, in particular in the range of 5-50, more in particular in the range of 8-30. In a specific embodiment m is at least 4, at least 10, at least 15 or at least 20.

The coupling product P—$W_v$-$AA_n$-$AA_m$ is subject to a cleavage reaction wherein the peptide $W_{v-1}$-$AA_n$-$AA_m$ is formed. Typically, cleavage is accomplished under addle conditions. If v−1>0, thereafter a group P is coupled to the W at the N-terminal position of the peptide $W_{v-1}$-$AA_n$-$AA_m$, to form P—$W_{v-1}AA_nAA_m$ after which P—W is cleaved. This is then repeated till the peptide represented by formula $AA_n$-$AA_m$ is obtained.

Accordingly, the present invention relates to a method for synthesising a peptide comprising the sequence His-X-Glu-Gly-Thr-Phe-Thr-Ser-Asp-Val-Ser-Ser-Tyr-Leu-Glu-Gly-Gln-Ala-Ala-Y-Glu-Phe-Ile-Ala-Trp-Leu-Val-Z-Gly-Arg-Gly (SEQ ID NO: 4), wherein
X is Ala or an α-amino-isobutyric acid (Aib) residue;
Y is Lys, which Lys has a free side-chain ε-amino group (i.e. a non-derivatised lysine residue), or whose Lys side-chain ε-amino group is protected with a protective group, or whose Lys side-chain ε-amino group is functionalized with an amino acid or another functional group;
Z is Arg or Lys;
the method comprising enzymatically coupling
(c) a first peptide C-terminal ester or thioester fragment comprising the sequence His-X-Glu-Gly-Thr-Phe-Thr-Ser-Asp-Val-Ser-(thio)ester (SEQ ID NO: 11), and
(d) a second peptide nucleophile fragment having an N-terminally unprotected amine comprising the sequence H-Ser-Tyr-Leu-Glu-Gly-Gln-Ala-Ala-Y-Glu-Phe-Ile-Ala-Trp-Leu-Val-Z-Qy-Arg-Gly (SEQ ID NO: 12);
which enzymatic coupling is catalyzed by a ligase, wherein said ligase is a subtilisin BPN' variant or a homologue thereof having at least 80%, or 85%, or 90%, preferably 95%, sequence identity. Preferably the ligase is a subtilisin BPN' variant having a deletion of the amino adds corresponding to positions 75-83, the mutation S221C and one or more further mutations, preferably at least 3 further mutations, in particular 5-8 further mutations, at amino acid positions corresponding to M222, Y217, P225, F189, N218, E156, G166 and N62 of wild-type subtilisin BPN' (mature), whereof most preferably one mutation is at P225.

In a particularly advantageous embodiment the ligase used in the method according to the invention is a subtilisin BPN' variant or a homologue thereof having at least 80%, or 85%, or 90%, preferably 95%, sequence identity with SEQ ID NO 14, comprising the mutations Q2K, S3C, P5S, S9A, I31L, K43N, M50F, A73L, Δ75-83, E156S, G166S, G169A, S188P, Q206C, N212G, Y217H, S221C, M222P, P225N, T254A, and Q271E, optionally comprising a His tag.

In another preferred embodiment the ligase used in the method according to the invention is a subtilisin BPN' variant with SEQ ID NO 3, or a homologue thereof having at least 80%, or 85%, or 90%, preferably 95%, sequence identity, comprising the mutations Q2K, S3C, P5S, S9A, I31L, K43N, M50F, N62A, A73L, Δ75-83, E156N, G166E, G169A, S188P, F189W, Q206C, N212G, Y217H, N218D, S221C, M222P, P225N, T254A, Q271E, optionally comprising a His tag.

SEQ ID N014 shows a subtilisin BPN' variant (for use) according to the invention with deletion of the $Ca^{2+}$ binding loop, S221C and further mutations. The His tag was included for facilitating purification and is not needed for ligase activity.

All the ligases described are also embodiments of the invention, preferably those specified by SEQ ID NO 14 and SEQ ID NO 3 and homologues thereof having at least 80%, or 85%, or 90%, preferably 95%, sequence identity.

In a preferred embodiment the method is further characterised by Y being a Lys, of which the side-chain ε-amino group is functionalized with a functional group, selected from the group consisting of γ-Glu-OH, Pal-γ-Glu-OH, AEEA-AEEA-γ-Glu-OH and AEEA-AEEA-γ-Glu-N-17-carboxyheptadecanoyl-OH, wherein Pal is palmitoyl and AEEA-AEEA is -2-[2-(2-aminoethoxy)ethoxy]acetyl-2-[2-(2-aminoethoxy)ethoxy]acetyl.

In an even more preferred embodiment said Y is Lys(γ-Glu-OH), Lys(AEEA-AEEA-γ-Glu-OH), Lys(Pal-γ-Glu-OH) or Lys(AEEA-AEEA-γ-Glu-17-carboxyheptadecanoyl-OH).

With the term "peptide fragment" or "fragment" is meant a peptide with a partial amino add sequence, with reference to a longer peptide with a defined sequence.

The invention will now be illustrated by the following examples, without being limited thereto.

EXAMPLES

Production of Ligases

Mutagenesis, Cloning and Expression

SEQ ID NO 1 shows the wild type gene coding for subtilisin BPN' amino acids −107 to 275. Herein the codons coding for amino acids −107 to −1 are present. These amino acids comprise the signal sequence, the pre-sequence and a pro sequence which are cleaved off upon full maturation. SEQ ID NO 2 shows the mature wild type subtilisin BPN' (i.e. without the amino acids −107 to −1). The ligase used for the Examples was as shown in SEQ ID NO: 3. Compared to the mature wild type subtilisin BPN', this ligase had the mutations Q2K, S3C, P5S, S9A, I31L, K43N, M50F, N62A, A73L, Δ75-83, E156N, G166E, G169A, S188P, F189W, Q206C, N212G, Y217H, N218D, S221C, M222P, P225N, T254A, and Q271E. Further, in order to facilitate a fast and efficient purification after amino acid 275 a C-terminal His-tag is attached as shown in SEQ ID NO 3. The corresponding amino acid sequence is numbered according to the subtilisin BPN' numbering scheme. Thus, in order to maintain the subtilisin BPN' numbering for used ligases the numbering jumps from 74 to 83.

The gene coding for the ligase used for the following synthesis examples was obtained from GenScript. The genes were cloned (by GenScript) into a pUB-110 E. coli-B. subtilis shuttle vector (pBES) using the MluI and BamHI site based vector. In the shuttle vector, the expression of the gene is under the control of the aprE promoter. The vector contained the pUB ori of replication for Bacillus and a kanamycin resistance marker. The vector also contained the ColE1 ori of replication and an ampicillin resistance marker for maintenance in E. coli. The resulting plasmid pBES-ligaseHIS was propagated in E. coli TOP10 and transformed into B. subtilis GX4935 (trpC2 metB10 lys-3 ΔnprE ΔaprE).

Production and Purification of the Ligases

A single microbial colony of B. subtilis containing a plasmid with the subtilisin variant gene of interest was inoculated in 5 mL LB with kanamycin (10 μg/mL) at 37° C. in a shaking incubator. To the 30 mL Terrific Broth supplemented with antibiotic (kanamycin 10 μg/mL) and amino acids (100 mg/L Trp, 100 mg/L Met and 100 mg/L Lys) 0.6 mL of the overnight culture was added. The cells were grown for 48 h at 37° C. in a shaking incubator (200 rpm). The cells were harvested by centrifugation (15 min, 4,000 rpm, 4° C.). The medium (30 mL) was decanted and concentrated on an Sartorius Vivaspin 15R unit (15 mL, 10 kDa MW cut-off) in two centrifugation steps (15 min, 4000 rpm, 4° C.). The concentrated medium (0.5 mL) was then exchanged for buffer A (25 mM Tricine, pH 7.5, 0.5 M NaCl) in three washing/concentrating steps (14 mL buffer A, 10 min, 4,000 rpm, 4° C.). For His-tag purification Talon resin (2.5 mL, Clonetech) was added to a plastic column cartridge. The resin was washed with 20 mL MilliQ water and equilibrated with 20 mL of buffer A. The crude enzyme was loaded on the column and washed with 5 mL buffer A. The enzyme was eluted with 15 mL buffer B (25 mM Tricine, pH 7.5, 0.5 M NaCl, 500 mM imidazole). The elute was concentrated on Sartorius Vivaspin 15R (15 mL, 10 kDa MW cut-off) by centrifugation (15 min, 4000 rpm, 4° C.) and the buffer was exchanged to 25 mM Tricine, pH 7.5 in three washing/concentrating steps (15 mL buffer, 10 min, 4,000 rpm, 4° C.).

The purity of the protein was analyzed by SDS-PAGE and the enzyme concentration was determined as described in WO2016056913 (A1). The purity was more than 90%. The obtained aqueous solution (25 mM Tricine, pH 7.5) containing about 2 mg/mL of the obtained enzyme was used as such for the oligopeptide fragment condensations.

Enzymatic Fragment Condensation Examples

Materials and Methods

Unless stated otherwise, chemicals were obtained from commercial sources and used without further purification. In all enzymatic fragment condensations the ligase of SEQ ID:3 was used. Analytical HPLC was performed on an Agilent 1260 infinity Liquid Chromatograph, using a reversed-phase column (Phenomenex, C18.5 μm particle size, 250*4.6 mm) at 40° C. UV detection was performed at 220 nm using a UV-VIS 204 Linear spectrometer. The gradient program was: 0-25 min linear gradient ramp from 5% to 98% eluent B and from 25.1-30 min 5% eluent B (eluent A: 0.5 mL/L methane sulfonic acid (MSA) in $H_2O$, eluent B 0.5 mL/L MSA in acetonitrile). The flow was 1 mL/min from 0-25.1 min and 2 mL/min from 25.2-29.8 min, then back to 1 mL/min until stop at 30 min. Injection volumes were 10 μL. Preparative HPLC was performed on a Varian PrepStar system using a stationary-phase column (Phenomenex, C18.10 μm particle size, 250×50 mm). LC-MS was performed on an Agilent 1200 series Liquid Chromatograph, using a reversed-phase column (Phenomenex, C18, 5 μm particle size, 150×4.6 mm) at 40° C. UV detection and gradient program were as described for analytical HPLC. The molecular weights were determined using an Agilent 6130 quadruple LC/MS system.

Protocol 1: Synthesis of Fmoc-Glycolic Acid

Tert-butyl 2-hydroxy-acetate (2.5 g) was dissolved in a mixture of pyridine (15 ml) and dichloromethane (DCM, 30 ml). Then Fmoc-chloride (5 g) in dry DCM (15 ml) was added drop wise at 0° C. The reaction mixture was stirred at room temperature for 24 hours. The solvent was removed under vacuum and the residue was redissolved in DCM (40 ml), washed with 1M sodium bicarbonate solution (20 mL) twice, brine solution (20 ml) twice, dried over anhydrous magnesium sulfate and concentrated. The obtained Fmoc-glycolic add tert-butyl ester (4 g) was dissolved in trifluoroacetic acid (TFA), triisopropylsilane (TIS) and water (95/2.5/2.5, v/v/v, 15 mL) and stirred for 120 min. The solvent was removed under vacuum and the viscous residue was redissolved in 5% sodium bicarbonate solution (150 ml), washed with diethyl ether (75 ml) 3 times. The aqueous solution was then mixed with ethyl acetate (45 mL) and acidified with 40% phosphoric add to pH=2 at 0° C. The organic layer was collected and dried with anhydrous magnesium sulfate. The solvent was removed under vacuum to give the final product Fmoc-glycolic acid (Fmoc-GA).

Protocol 2: Synthesis of Oligopeptide-OCam-Leu-OH Esters 1 gram of preloaded Fmoc-Leu-Wang resin (with a loading of 0.81 mmol/gram) was washed with DCM (2×2 min, 10 mL) and N,N'-dimethylformamide (DMF, 2×2 min, 10 mL) and Fmoc-deprotected using piperidine/DMF (1/5, v/v, 2×8 min, 10 mL). After washing with DMF (6×2 min, 10 mL), Fmoc-GA (4 equiv.) was coupled to the resin using 2-(1H-benzotriazol-1-yl)-1,1,3,3-tetramethyluronium hexafluorophosphate (HBTU, 4 equiv.), OxymaPure (4 equiv.) and di-isopropylethylamine (DIPEA, 8 equiv.) in DMF (45 min, 10 mL). After washing with DMF (2×2 min, 10 mL) the resin was Fmoc-deprotected using piperidine/DMF (1/5, v/v, 2×8 min, 10 mL). The Cam-Leu-OH ester was formed by coupling of the first Fmoc-protected amino acid using 4 equiv. Fmoc-Xxx-OH, 4 equiv. N,N'-diisopropylcarbodiimide (DIC) and 0.1 equiv. 4-dimethylaminopyridine (DMAP) in DMF (2×60 min, 10 mL). Here and in other parts of this disclosure 'Xxx' stands for one amino acid (variable as indicated in the sequences in the examples below). For the Semaglutide starting material a commercially available Fmoc-Aib-OH building block was used.

After washing with DMF (6×2 min, 10 mL), standard SPPS protocols were followed to elongate the peptide (Weng C. Chan and Peter White, OUP Oxford, 2000). Cleavage from the resin and side-chain deprotection was performed using a mixture of TFA/TIS/water (95/2.5/2.5, v/v/v, 15 mL) for 120 min. The crude peptide was precipitated using methyl tert-butyl ether (MTBE)/n-heptanes (1/1, v/v, 50 mL). The precipitated peptide was collected by centrifugation and washed twice with MTBE/n-heptanes (1/1, v/v, 50 mL) followed by lyophilization from acetonitrile/water (1/1, v/v, 50 mL). The crude products were purified by preparative HPLC followed by lyophilization of the pure fractions.

As described above, but then on a preloaded Fmoc-Arg(Pbf)-Rink resin (with a loading of 0.62 mmol/gram), several alternative peptide Cam-esters were prepared, i.e. H-$^1$His-$^2$Ala-$^3$Glu-$^4$Gly-$^6$Phe-$^7$Thr-$^8$Ser-$^9$Asp-$^{10}$Val-$^{11}$Ser-OCam-Phe-Arg-NH$_2$, H-$^1$His-$^2$Ala-$^3$Glu-$^4$Gly-$^5$Thr-$^6$Phe-$^7$Thr-$^8$Ser-$^9$Asp-$^{10}$Val-$^{11}$Ser-OCam-Leu-Arg-NH$_2$ and H-$^1$His-$^2$Ala-$^3$Glu-$^4$Gly-$^5$Thr-$^6$Phe-$^7$Thr-$^8$Ser-$^9$Asp-$^{10}$Val-$^{11}$Ser-OCam-Trp-Arg-NH$_2$(SEQ ID NO: 11).

Protocol 3: Synthesis of Oligopeptide C-Terminal Acid Nucleophiles 1 gram of preloaded Fmoc-Gly-Wang resin (with a loading of 0.30 mmol/gram) was washed with DCM (2×2 min, 10 mL) and DMF (2×2 min, 10 mL) and Fmoc-deprotected using piperidine/DMF (1/5, v/v, 2×8 min, 10 mL). Standard SPPS protocols were followed to elongate the peptide (Weng C. Chan and Peter White, OUP Oxford, 2000). Cleavage from the resin and side-chain deprotection was performed using a mixture of TFA/TIS/water (95/2.5/2.5, v/v/v, 15 mL) for 120 min. The crude peptide was precipitated using MTBE/n-heptanes (1/1, v/v, 50 mL). The precipitated peptide was collected by centrifugation and washed twice with MTBE/n-heptanes (1/1, v/v, 50 mL) followed by lyophilization from acetonitrile/wafer (1/1, v/v, 50 mL). The crude products were purified by preparative HPLC followed by lyophilization of the pure fractions.

Protocol 4: PTC Protection of H-Gly-1His-2Ala-3Glu-4Gly-5Thr-6Phe-7Thr-8Ser-9Asp-10Val-11Ser-OCam-Leu-OH 100 mg of H-Gly-1 His-2Ala-3Glu-4Gly-5Phe-7Thr-8Ser-9Asp-10Val-11 Ser-OCam-Leu-OH (Gly+SEQ ID NO:11) was dissolved in 10 mL pyridine/water (1/1, v/v). To this mixture 25 mg of phenylisothiocyanate was added and the solution was stirred at ambient temperature for 14 hours. The crude reaction mixture was diluted with 50 mL water and washed three times with 50 mL dichloromethane (DCM). The water layer was purified by preparative HPLC followed by lyophilization of the pure fractions giving the PTC-Gly protected peptide.

Protocol 5: Synthesis of γ-Glu or Pal-γ-Glu Containing Peptides

General protocol 3 was followed using commercially available Fmoc-Lys(Boc-γ-Glu-O$^t$Bu)—OH or Fmoc-Lys(Pal-γ-Glu-O$^t$Bu)—OH building blocks.

Protocol 6: Synthesis of the Semaglutide fragment H-$^{12}$Ser-$^{13}$Tyr-$^{14}$Leu-$^{15}$Glu-$^{16}$Gly-$^{17}$Gln-$^{18}$Ala-$^{19}$Ala-$^{20}$Lys(AEEA-AEEA-γ-Glu-N-17-carboxyheptadecanoyl-OH)-$^{21}$Glu-$^{22}$Phe-$^{23}$Ile-$^{24}$Ala-$^{25}$Trp-$^{26}$Leu-$^{27}$Val-$^{28}$Arg-$^{29}$Gly-$^{30}$Arg-$^{31}$Gly-OH (SEQ ID NO:12).

General protocol 3 was followed using a commercially available Fmoc-$^{20}$Lys(Mtt)-OH and Boc-$^{12}$Ser($^t$Bu)—OH building block. After SPPS of the Boc-12-31-Wang fragment the Mtt protecting group was removed using 10 mL of TIS/TFA/DCM (1/1/48, v/v/v, 3×15 min). Standard SPPS procedures were used for the coupling of Fmoc-AEEA-OH (twice), Fmoc-Glu-O$^t$Bu, and 17-carboxyheptadecanoyl-O$^t$Bu. Cleavage from the resin and side-chain deprotection was performed using a mixture of TFA/TIS/water (95/2.5/2.5, v/v/v, 15 mL) for 120 min. The crude peptide was precipitated using MTBE/n-heptane (1/1, v/v, 50 mL). The precipitated peptide was collected by centrifugation and washed twice with MTBE/n-heptane (1/1, v/v, 50 mL) followed by lyophilization from acetonitrile/water (1/1, v/v, 50 mL). The crude products were purified by preparative HPLC followed by lyophilization of the pure fractions.

Example 1 (Reference)

Enzymatic Synthesis of the Liraglutide Precursor H-Liraglutide-1-31-OH Using a 13-mer+18-mer Approach.

In an HPLC vial, 6 mg of H-$^1$His-$^2$Ala-$^3$Glu-$^4$Gly-$^5$Thr-$^6$Phe-$^7$Thr-8Ser-$^9$Asp-$^{10}$Val-$^{11}$Ser-$^{12}$Ser-$^{13}$Tyr-OCam-Leu-OH (SEQ ID NO: 9) and 9 mg of H-$^{14}$Leu-$^{15}$Glu-$^{16}$Gly-$^{17}$Gln-$^{18}$Ala-$^{19}$Ala-$^{20}$Lys-$^{21}$Glu-$^{22}$Phe-$^{23}$Ile-$^{24}$Ala-$^{25}$Trp-$^{26}$Leu-$^{27}$Val-$^{28}$Arg-$^{29}$Gly-$^{30}$Arg-$^{31}$Gly-OH (SEQ ID NO:10) were dissolved in 800 μL 2M aqueous guanidinium chloride. To this mixture, 50 μL 1M tricine buffer pH 9.0 was added and the pH was adjusted to 8.3 using a 4M NaOH solution. Subsequently, 10 μL of TCEP (tris(2-carboxyethyl)phosphine) solution (100 mg/mL in water) and 100 μL of the ligase solution (10 mg/mL) were added. The mixture was left to react at ambient temperature. Every 15 minutes, 10 μL of the reaction mixture was withdrawn and quenched in 980 μL 5 vol % MSA in acetonitrile/water (2/1, v/v) and analysed using LC-MS.

After 90 minutes all Cam-ester starting material had been consumed, and the product and hydrolysis peaks were integrated. The ligation product H-1His-2Ala-3Glu-4Gly- 5Thr-6Phe-7Thr-8Ser-9Asp-10Val-11 Ser-12Ser-13Tyr-14Leu-15Glu-16Gly-17Gln-18Ala-19Ala-20Lys-21 Glu-22Phe-23Ile-24Ala-25Trp-26Leu-27Val-28Arg-29Gly-30Arg-31 Gly-OH (SEQ ID NO: 5) was 14 area % and the hydrolysed Cam-ester H-1His-2Ala-3Glu-4Gly-5Thr-6Phe-7Thr-8Ser-9Asp-10Val-11 Ser-12Ser-13Tyr-OH (residues 1-13 of SEQ ID NO: 9) was 86 area %.

The product H-Liraglutide-1-31-OH could be obtained by preparative HPLC followed by lyophilization of the pure fractions.

Example 2 (Reference)

Enzymatic Synthesis of the Liraglutide Precursor H-Liraglutide-1-31-OH Using a 9-mer+22-mer Approach.

In an HPLC vial, 6 mg of H-$^1$His-$^2$Ala-$^3$Glu-$^4$Gly-$^5$Thr-$^6$Phe-$^7$Thr-$^8$Ser-$^9$Asp-OCam-Leu-OH (residues 1-9 of SEQ ID NO: 5) and 10 mg of H-$^{10}$Val-$^{11}$Ser-$^{12}$Ser-$^{13}$Tyr-$^{14}$Leu-$^{15}$Glu-$^{16}$Gly-$^{17}$Gln-$^{18}$Ala-$^{19}$Ala-$^{20}$Lys-$^{21}$Glu-$^{22}$Phe-$^{23}$Ile-$^{24}$Ala-$^{25}$Trp-$^{26}$Leu-$^{27}$Val-$^{28}$Arg-$^{29}$Gly-$^{30}$Arg-$^{31}$Gly-OH (residues 10-31 of SEQ ID NO: 5) were dissolved in 800 μL 2M aqueous guanidinium chloride. To this mixture, 50 μL 1M tricine buffer pH 9.0 was added and the pH was adjusted to 8.3 using a 4M NaOH solution. Subsequently, 10 μL of TCEP solution (100 mg/mL in water) and 100 μL of ligase solution (10 mg/mL) were added. The mixture was left to react at ambient temperature. Every 15 minutes, 10 μL of the reaction mixture was quenched in 980 μL 5 vol % MSA in acetonitrile/water (2/1, v/v) and analysed using LC-MS.

After 300 minutes all Cam-ester starting material was consumed, and the product and hydrolysis peaks were integrated. The ligation product H-$^1$His-$^2$Ala-$^3$Glu-$^4$Gly-$^5$Thr-$^6$Phe-$^7$Thr-$^8$Ser-$^9$Asp-$^{10}$Val-$^{11}$Ser-$^{12}$Ser-$^{13}$Tyr-$^{14}$Leu-$^{15}$Glu-$^{16}$Gly-$^{17}$Gln-$^{18}$Ala-$^{19}$Ala-$^{20}$Lys-$^{21}$Glu-$^{22}$Phe-$^{23}$Ile-$^{24}$Ala-$^{25}$Trp-$^{26}$Leu-$^{27}$Val-$^{28}$Arg-$^{29}$Gly-$^{30}$Arg-$^{31}$Gly-OH (SEQ ID NO: 5) was 8 area % and the hydrolysed Cam-ester H-$^1$His-$^2$Ala-$^3$Glu-$^4$Gly-$^5$Thr-$^6$Phe-$^7$Thr-$^8$Ser-$^9$Asp-OH (residues 1-9 of SEQ ID NO: 5) was 92 area %.

The product H-Liraglutide-1-31-OH could be obtained by preparative HPLC followed by lyophilization of the pure fractions.

Example 3: Enzymatic Synthesis of H-Liraglutide-1-31-OH Using an 11-mer+20-mer Approach In an HPLC vial, 6 mg of H-$^1$His-$^2$Ala-$^3$Glu-$^4$Gly-$^5$Thr-$^6$Phe-$^7$Thr-$^8$Ser-$^9$Asp-$^{10}$Val-$^{11}$Ser-OCam-Leu-OH (residues 1-11 of SEQ ID NO: 5) and 10 mg of H-$^{12}$Ser-$^{13}$Tyr-$^{14}$Leu-$^{15}$Glu-$^{16}$Gly-$^{17}$Gln-$^{18}$Ala-$^{19}$Ala-$^{20}$Lys-$^{21}$Glu-$^{22}$Phe-$^{23}$Ile-$^{24}$Ala-$^{25}$Trp-$^{26}$Leu-$^{27}$Val-$^{28}$Arg-$^{29}$Gly-$^{30}$Arg-$^{31}$Gly-OH (residues 12-31 of SEQ ID NO: 5) were dissolved in 800 μL 2M aqueous guanidinium chloride. To this mixture, 50 μL 1M tricine buffer pH 9.0 was added and the pH was adjusted to 8.3 using a 4M NaOH solution. Subsequently, 10 μL of TCEP solution (100 mg/mL in water) and 100 μL of ligase solution (10 mg/mL) were added. The mixture was left to react at ambient temperature. Every 15 minutes, 10 μL of the reaction mixture was withdrawn and quenched in 980 μL 5 vol % MSA in acetonitrile/water (2/1, v/v) and analysed using LC-MS.

After 180 minutes all Cam-ester starting material had been consumed, and the product and hydrolysis peaks were integrated. The ligation product H-$^1$His-$^2$Ala-$^3$Glu-$^4$Gly-$^5$Thr-$^6$Phe-$^7$Thr-$^8$Ser-$^9$Asp-$^{10}$Val-$^{11}$Ser-$^{12}$Ser-$^{13}$Tyr-$^{14}$Leu-$^{15}$Glu-$^{16}$Gly-$^{17}$Gln-$^{18}$Ala-$^{19}$Ala-$^{20}$Lys-$^{21}$Glu-$^{22}$Phe-$^{23}$Ile-$^{24}$Ala-$^{25}$Trp-$^{26}$Leu-$^{27}$Val-$^{28}$Arg-$^{29}$Gly-$^{30}$Arg-$^{31}$Gly-OH (SEQ ID NO: 5) was 96 area % and the hydrolysed Canister H-$^1$His-$^2$Ala-$^3$Glu-$^4$Gly-$^5$Thr-$^6$Phe-$^7$Thr-$^8$Ser-$^9$Asp-$^{10}$Val-$^{11}$Ser-$^{12}$Ser-$^{13}$Tyr-OH (residues 1-13 of SEQ ID NO: 5) was 4 area %.

The product H-Liraglutide-1-31-OH could be obtained by preparative HPLC followed by lyophilization of the pure fractions.

It is thus shown that a method according to the invention unexpectedly provides the desired coupled product (i.e. H-Liraglutide-1-31-OH, the peptide having the amino acid sequence of Liraglutide without derivatization at $^{20}$Lys) at a much higher yield than in a comparable method wherein the coupling site for the C-terminal (thio)ester and peptide nucleophile is two amide bonds towards the C-terminus or N-terminus of the H-Liraglutide-1-31-OH.

Example 4: Enzymatic Synthesis of PTC-Gly-Liraglutide-1-31-[$^{20}$Lys(γ-Glu)]-OH Using an 11-mer+ 20-mer Approach In an HPLC vial, 6 mg of PTC-Gly-$^1$His-$^2$Ala-$^3$Glu-$^4$ay-$^5$Thr-6Phe-$^7$Thr-8Ser-$^9$Asp-$^{10}$Val-$^{11}$Ser-OCam-Leu-OH (residues 1-11 of SEQ ID NO: 6) and 10 mg of H-$^{12}$Ser-$^{13}$Tyr-$^{14}$Leu-$^{15}$Glu-$^{16}$ay-$^{17}$Gln-$^{18}$Ala-$^{19}$Ala-$^{20}$Lys(γ-Glu)-$^{21}$Glu-$^{22}$Phe-$^{23}$Ile-$^{24}$Ala-$^{25}$Trp-$^{26}$Leu-$^{27}$Val-$^{28}$Arg-$^{29}$Gly-$^{30}$Arg-$^{31}$Gly-OH (residues 12-31 of SEQ ID NO: 6) were dissolved in 800 μL 2M aqueous guanidinium chloride.

To this mixture, 50 μL 1M tricine buffer pH 9.0 was added and the pH was adjusted to 8.3 using a 4M NaOH solution. Subsequently, 10 μL of TCEP solution (100 mg/mL in water) and 100 μL of ligase solution (10 mg/mL) were added. The mixture was left to react at ambient temperature. Every 15 minutes, 10 μL of the reaction mixture was withdrawn and quenched in 980 μL 5 vol % MSA in acetonitrile/water (2/1, v/v) and analysed using LC-MS.

After 180 minutes all Cam-ester starting material had been consumed, and the product and hydrolysis peaks were integrated. The ligation product PTC-Gly-$^1$His-$^2$Ala-$^3$Glu-$^4$Gly-$^5$Thr-$^6$Phe-$^7$Thr-$^8$Ser-$^9$Asp-$^{10}$Val-$^{11}$Ser-$^{12}$Ser-$^{13}$Tyr-$^{14}$Leu-$^{15}$Glu-$^{16}$Gly-$^{17}$Gln-$^{18}$Ala-$^{19}$Ala-$^{20}$Lys(Y-Glu)-$^{21}$Glu-$^{22}$Phe-$^{23}$Ile-$^{24}$Ala-$^{25}$Trp-$^{26}$Leu-$^{27}$Val-$^{28}$Arg-$^{29}$Gly-$^{30}$Arg-$^{31}$Gly-OH (SEQ ID NO: 6) was 93 area % and the hydrolysed Cam-ester PTC-Gly-$^1$His-$^2$Ala-$^3$Glu-$^4$Gly-$^5$Thr-$^6$Phe-$^7$Thr-$^e$Ser-$^9$Asp-$^{10}$Val-$^{11}$Ser-OH (residues 1-11 of SEQ ID NO: 6) was 7 area %.

The product PTC-Gly-Liraglutide-1-31-[$^{20}$Lys(γGlu)]l-OH could be obtained by preparative HPLC followed by lyophilization of the pure fractions.

Example 5: Synthesis of H-Liraglutide-1-31-[$^{20}$Lys (Pal-γ-Glu)]-OH Using the PTC-Gly-Liraglutide-1-31-[$^{20}$Lys(γ-Glu)]-OH Precursor from Example 4

2 mg of PTC-Gly-$_1$His-$^2$Ala-$^3$Glu-$^4$Gly-$^5$Thr-$^6$Phe-$^7$Thr-$^8$Ser-$^9$Asp-$^{10}$Val-$^{11}$Ser-$^{12}$Ser-$^{13}$Tyr-$^{14}$Leu-$^{15}$Glu-$^{16}$Gly-$^{17}$Gln-$^{18}$Ala-$^{19}$Ala-$^{20}$Lys(γ-Glu)-$^{21}$Glu-$^{22}$Phe-$^{23}$Ile-$^{24}$Ala-$^{25}$Trp-$^{26}$Leu-$^{27}$Val-$^{28}$Arg-$^{29}$Gly-$^{30}$Arg-$^{31}$Gly-OH (SEQ ID NO: 6) was dissolved in 500 μL water and 500 μL pyridine. To this solution, 2 mg of palmitic acid N-hydroxy succinimide ester (Pal-OSu) was added and the mixture was left to react at ambient temperature for 5 hours followed by evaporation of the solvents in vacuo. The crude product PTC-Gly-$^1$His-$^2$Ala-$^3$Glu-$^4$Gly-$^5$Thr-$^6$Phe-$^7$Thr-$^8$Ser-$^9$Asp-$^{10}$Val-$^{11}$Ser-$^{12}$Ser-$^{13}$Tyr-$^{14}$Leu-$^{15}$Glu-$^{16}$Gly-$^{17}$Gln-$^{18}$Ala-$^{19}$Ala-$^{20}$Lys(Pal-γ-Glu)-$^{21}$Glu-$^{22}$Phe-$^{23}$Ile-$^{24}$Ala-$^{25}$Trp-$^{26}$Leu-$^{27}$Val-$^{28}$Arg-$^{29}$Gly-$^{30}$Arg-$^{31}$Gly-OH (SEQ ID NO: 6) was dissolved in 5 vol % trifluoroacetic acid in water for cleavage (deprotection) of the PTC-Gly group.

After completion (15 min), the product H-$^1$His-$^2$Ala-$^3$Glu-$^4$Gly-$^5$Thr-$^6$Phe-$^7$Thr-$^8$Ser-$^9$Asp-$^{10}$Val-$^{11}$Ser-$^{12}$Ser-$^{13}$Tyr-$^{14}$Leu-$^{15}$Glu-$^{16}$Gly-$^{17}$Gln-$^{18}$Ala-$^{19}$Ala-$^{20}$Lys(Pal-γ-Glu)-$^{21}$Glu-$^{22}$Phe-$^{23}$Ile-$^{24}$Ala-$^{25}$Trp-$^{26}$Leu-$^{27}$Val-$^{28}$Arg-$^{29}$Gly-$^{30}$Arg-$^{31}$Gly-OH (SEQ ID NO: 6) was obtained and purified by preparative HPLC followed by lyophilization of the pure fractions.

Example 6: Enzymatic Synthesis of H-Liraglutide-1-31-[$^{20}$Lys(Pal-γ-Glu)]-OH Using an 11-mer+20-mer Approach (Pal=Palmitoyl)

In an HPLC vial, 6 mg of H-$^1$His-$^2$Ala-$^3$Glu-$^4$Gly-$^5$Thr-$^6$Phe-$^7$Thr-$^8$Ser-$^9$Asp-$^{10}$Val-$^{11}$Ser-OCam-Leu-OH (residues 1-11 of SEQ ID NO:6) and 10 mg of H-$^{12}$Ser-$^{13}$Tyr-$^{14}$Leu-$^{15}$Glu-$^{16}$Gly-$^{17}$Gln-$^{18}$Ala-$^{19}$Ala-$^{20}$Lys(Pal-γ-Glu)$^{21}$Glu-$^{22}$Phe-$^{23}$Ile-$^{24}$Ala-$^{25}$Trp-$^{26}$Leu-$^{27}$Val-$^{28}$Arg-$^{29}$Gly-$^{30}$Arg-$^{31}$Gly-OH (residues 12-31 of SEQ ID NO:6) were dissolved in 950 µL water. To this mixture, 50 µL 1M tricine buffer pH 9.0 was added and the pH was adjusted to 8.1 using a 3M NaOH solution. Subsequently, 10 µL of TCEP solution (100 mg/mL in water) and 100 µL of ligase solution (10 mg/mL) were added. The mixture was left to react at ambient temperature. Every 15 minutes, 10 µL of the reaction mixture was withdrawn and quenched in 980 µL 5 vol % MSA in acetonitrile/water (2/1, v/v) and analysed using LC-MS.

After 180 minutes all Cam-ester starting material had been consumed and the product and hydrolysis peaks were integrated. The ligation product H-$^1$His-$^2$Ala-$^3$Glu-$^4$Gly-$^5$Thr-$^6$Phe-$^7$Thr-$^8$Ser-$^9$Asp-$_{10}$Val-$^{11}$Ser-$^{12}$Ser-$^{13}$Tyr-$^{14}$Leu-$^{15}$Glu-$^{16}$Gly-$^{17}$Gln-$^{18}$Ala-$^{19}$Ala-$^{20}$Lys(Pal-γ-Glu)-$^{21}$Glu-$^{22}$Phe-$^{23}$Ile-$^{24}$Ala-$^{25}$Trp-$^{26}$Leu-$^{27}$Val-$^{28}$Arg-$^{29}$Gly-$^{30}$Arg-$^{31}$Gly-OH (SEQ ID NO: 6) was 95 area % and the hydrolysed Gamester H-$^1$His-$^2$Ala-$^3$Glu-$^4$Gly-$^5$Thr-$^6$Phe-$^7$Thr-$^8$Ser-$^9$Asp-$^{10}$Val-$^{11}$Ser-OH (residues 1-11 of SEQ ID NO: 6) was 5 area %.

This Example shows that the present invention allows the direct synthesis of Liraglutide in a single enzymatic coupling step in high yield.

An identical ligation reaction as described above was performed except for using several alternative peptide Cam-esters, i.e. (1) H-$^1$His-$^2$Ala-$^3$Glu-$^4$Gly-$^5$Thr-$^6$Phe-$^7$Thr-$^8$Ser-$^9$Asp-$^{10}$Val-$^{11}$Ser-OCam-Phe-Arg-NH$_2$ (residues 1-11 of SEQ ID NO: 6), (2) H-$^1$His-$^2$Ala-$^3$Glu-$^4$Gly-$^5$Thr-$^6$Phe-$^7$Thr-$^8$Ser-$^9$Asp-$^{10}$Val-$^{11}$Ser-OCam-Leu-Arg-NH$_2$ (residues 1-11 of SEQ ID NO: 6) and (3) H-$^1$His-$^2$Ala-$^3$Glu-$^4$Gly-$^5$Thr-$^6$Phe-$^7$Thr-$^8$Ser-$^9$Asp-$^{10}$Val-$^{11}$Ser-OCam-Trp-Arg-NH$_2$ (residues 1-11 of SEQ ID NO: 6). In general the reactions proceeded faster than for the H-$^1$His-$^2$Ala-$^3$Glu-$^4$Gly-$^5$Thr-$^6$Phe-$^7$Thr-$^8$Ser-$^9$Asp-$^{10}$Val-$^{11}$Ser-OCam-Leu-OH (residues 1-11 of SEQ ID NO: 6) (180 min) ester resulting in a complete conversion after 80 min for (1), 100 min for (2) and 85 min for (3).

Example 7: Synthesis of H-Liraglutide-1-31-[$^{20}$Lys(Pal-γ-Glu)]-OH from the Enzymatically Synthesized Precursor H-Liraglutide-1-31-OH of Example 3

To the precursor H-$^1$His-$^2$Ala-$^3$Glu-$^4$Gly-$^5$Thr-$^6$Phe-$^7$Thr-$^8$Ser-$^9$Asp-$^{10}$Val-$^{11}$Ser-$^{12}$Ser-$^{13}$Tyr-$^{14}$Leu-$^{15}$Glu-$^{16}$Gly-$^{17}$Gln-$^{18}$Ala-$^{19}$Ala-$^{20}$Lys-$^{21}$Glu-$^{22}$Phe-$^{23}$Ile-$^{24}$Ala-$^{25}$Trp-$^{26}$Leu-$^{27}$Val-$^{28}$Arg-$^{29}$Gly-$^{30}$Arg-$^{31}$Gly-OH (SEQ ID NO: 6), the Pal-γ-Glu moiety is coupled to obtain the product H-$^1$His-$^2$Ala-$^3$Glu-$^4$Gly-$^5$Thr-$^6$Phe-$^7$Thr-$^8$Ser-$^9$Asp-$^{10}$Val-$^{11}$Ser-$^{12}$Ser-$^{13}$Tyr-$^{15}$Glu-$^{16}$Gly-$^{17}$Gln-$^{18}$Ala-$^{19}$Ala-$^{20}$Lys(Pal-γ-Glu)-$^{21}$Glu-$^{22}$Phe-$^{23}$Ile-$^{24}$Ala-$^{25}$Trp-$^{26}$Leu-$^{27}$Val-$^{28}$Arg-$^{29}$-Gly-$^{30}$Arg-$^{31}$Gly-OH (SEQ ID NO: 6) using protocols described in U.S. Pat. No. 6,451,974 B1.

Example 8: Synthesis of H-Semaglutide-1-31-[$^{20}$Lys(AEEA-AEEA-γ-Glu-N-17-carboxyheptadecanoyl-OH)]-OH Using an 11-mer+20-mer Approach In an HPLC vial, 6 mg of H-$^1$His-$^2$Aib-$^3$Glu-$^4$Gly-$^5$Thr-$^6$Phe-$^7$Thr-$^8$Ser-$^9$Asp-$^{10}$Val-$^{11}$Ser-OCam-Leu-OH (residues 1-11 of SEQ ID NO: 7) and 10 mg of H-$^{12}$Ser-$^{13}$Tyr-$^{14}$Leu-$^{15}$Glu-$^{16}$Gly-$^{17}$Gln-$^{18}$Ala-$^{19}$Ala-$^{20}$Lys(AEEA-AEEA-γ-Glu-N-17-carboxyheptadecanoyl-OH)-$^{21}$Glu-$^{22}$Phe-$^{23}$Ile-$^{24}$Ala-$^{25}$Trp-$^{26}$Leu-$^{27}$Val-$^{28}$Arg-$^{29}$Gly-$^{30}$Arg-$^{31}$Gly-OH (residues 12-31 of SEQ ID NO: 7) were dissolved in 950 µL water. To this mixture, 50 µL 1M tricine buffer pH 9.0 was added and the pH was adjusted to 8.1 using a 3M NaOH solution. Subsequently, 10 µL of TCEP solution (100 mg/mL in water) and 100 µL of ligase solution (10 mg/mL) were added. The mixture was left to react at ambient temperature. Every 15 minutes, 10 µL of the reaction mixture was withdrawn and quenched in 980 µL 5 vol % MSA in acetonitrile/water (2/1, v/v) and analysed using LC-MS.

After 180 minutes all Cam-ester starting material had been consumed and the product and hydrolysis peaks were integrated. The ligation product H-$^1$His-$^2$Aib-$^3$Glu-$^4$Gly-$^5$Thr-$^6$Phe-$^7$Thr-$^8$Ser-$^9$Asp-$^{10}$Val-$^{11}$Ser-$^{12}$Ser-$^{13}$Tyr-$^{14}$Leu-$^{15}$Glu-$^{16}$Gly-$^{17}$Gln-$^{18}$Ala-$^{19}$Ala-$^{20}$Lys(AEEA-AEEA-γ-Glu-N-17-carboxyheptadecanoyl-OH)-$^{21}$Glu-$^{22}$Phe-$^{23}$Ile-$^{24}$Ala-$^{25}$Trp-$^{26}$Leu-$^{27}$Val-$^{28}$Arg-$^{29}$Gly-$^{30}$Arg-$^{31}$Gly-OH (SEQ ID NO: 7) was 96 area % and the hydrolysed Cam-ester H-$^1$His-$^2$Aib-$^3$Glu-$^4$Gly-$^5$Thr-$^6$Phe-$^7$Thr-$^8$Ser-$^9$Asp-$^{10}$Val-$^{11}$Ser-OH (residues 1-11 of SEQ ID NO: 7) was 4 area %.

This Example shows that the present invention allows the direct synthesis of Semaglutide in a single enzymatic coupling step in high yield.

Example 9: Enzymatic Synthesis of H-Liraglutide-1-31-OH Using an 11-mer+20-mer Approach with Enzyme Variant SEQ ID NO 14

In an HPLC vial, 10 mg of H-$^1$His-$^2$Ala-$^3$Glu-$^4$Gly-$^5$Thr-$^6$Phe-$^7$Thr-$^8$Ser-$^9$Asp-$^{10}$Val-$^{11}$Ser-OCam-Leu-OH (SEQ ID NO: 11) and 10 mg of H-$^{12}$Ser-$^{13}$Tyr-$^{14}$Leu-$^{15}$Glu-$^{16}$Gly-$^{17}$Gln-$^{18}$Ala-$^{19}$Ala-$^{20}$Lys-$^{21}$Glu-$^{22}$Phe-$^{23}$Ile-$^{24}$Ala-$^{25}$Trp-$^{26}$Leu-$^{27}$Val-$^{28}$Arg-$^{29}$Gly-$^{30}$Arg-$^{31}$Gly-OH (SEQ ID NO: 13) were dissolved in 500 µL 50 mM tricine buffer pH 9.0. The pH was adjusted to 8.3 using a 3 M NaOH solution. Subsequently, 10 µL of TCEP solution (100 mg/mL in water) and 100 µL of ligase solution (10 mg/mL) were added. The mixture was left to react at ambient temperature. Every 15 minutes, 10 µL of the reaction mixture was withdrawn and quenched in 980 µL 5 vol % MSA in acetonitrile/water (2/1, v/v) and analysed using LC-MS.

After 240 minutes all Cam-ester starting material had been consumed, and the product and hydrolysis peaks were integrated. The ligation product H-$^1$His-$^2$Ala-$^3$Glu-$^4$Gly-$^5$Thr-$^6$Phe-$^7$Thr-$^8$Ser-$^9$Asp-$_{10}$Val-$^{11}$Ser-$^{12}$Ser-$^{13}$Tyr-$^{14}$Leu-$^{15}$Glu-$^{16}$Gly-$^{17}$Gln-$^{18}$Ala-$^{19}$Ala-$^{20}$Lys-$^{21}$Glu-$^{22}$-Phe-$^{23}$Ile-$^{24}$-Ala-$^{25}$-Trp-$^{26}$Leu-$^{27}$Val-$^{28}$Arg-$^{29}$Gly-$^{30}$Arg-$^{31}$Gly-OH (SEQ ID NO: 5) was 92 area % and the hydrolysed Cam-ester H-$^1$His-$^2$Ala-$^3$Glu-$^4$Gly-$^5$Thr-$^6$Phe-$^7$Thr-$^8$Ser-$^9$Asp-$^{10}$Val-$^{11}$Ser-OH (residues 1-11 of SEQ ID NO: 5) was 8 area %.

The product H-Liraglutide-1-31-OH could be obtained by preparative HPLC followed by lyophilization of the pure fractions.

Example 10: Identification of Fragments Suitable for the Enzymatic Synthesis of Liraglutide Using Serine Endoprotease Derived from Subtilisin BPN' Variant with SEQ ID NO: 3 (C221S Mutated)

1 mg of liraglutide 1-31 (with and without the Pal-γ-Glu at the lysine in position 20) was dissolved in 1 mL of tricine buffer (50 mM, pH=8.0). To this mixture, 1 µL of endoprotease solution (1 mg/mL) was added and the reaction mixture was stirred at room temperature.

Hydrolytic activity was monitored by analysing samples every 30 min using LC-MS analysis.

For both peptides, the highest hydrolytic activity was observed at the bond between amino acid 25 and amino acid 26 (yielding the fragments 1-25+26-31), followed by hydrolytic activity at the bond between amino acid 5 and 6 (yielding the fragments 1-5+6-31). The goodness of a 25-mer+6-mer approach was tested in comparison EXAMPLE 11.

Example 11: Enzymatic Synthesis of the Liraglutide Precursor H-Liraglutide-1-31-OH Using in Parallel a 25-mer+6-mer Approach (Reference), 5-mer+26-mer Approach (Reference), or 11-mer+20-mer Approach (According to the Invention)

In an HPLC vial, 3 µmol of ester (1: H-$^1$His-$^2$Ala-$^3$Glu-$^4$Gly-$^5$Thr-$^6$Phe-$^7$Thr-$^8$Ser-$^9$Asp-$^{10}$Val-$^{11}$Ser-$^{12}$Ser-$^{13}$Tyr-$^{14}$Leu-$^{15}$Glu-$^{16}$Gly-$^{17}$Gln-$^{18}$Ala-$^{19}$Ala-$^{20}$Lys-(Pal-γ-Glu)-$^{21}$Glu-$^{22}$Phe-$^{23}$Ile-$^{24}$Ala-$^{25}$Trp-OCam-Leu-OH (residues of 1-25 of SEQ ID NO: 6), 2: H-$^1$His-$^2$Ala-$^3$Glu-$^4$Gly-$^5$Thr-OCam-Leu-OH (residues 1-5 of SEQ ID NO: 6) or 3: H-$^1$His-$^2$Ala-$^3$Glu-$^4$Gly-$^5$Thr-$^6$Phe-$^7$Thr-$^8$Ser-$^9$Asp-$^{10}$Val-$^{11}$Ser-OCam-Leu-OH (residues 1-11 of SEQ ID NO: 6)) and 2 µmol amine (1: H-$^{26}$Leu-$^{27}$Val-$^{28}$Arg-$^{29}$Gly-$^{30}$Arg-$^{31}$Gly-OH (residues 26-31 of SEQ ID NO: 6), 2: H-$^6$Phe-$^7$Thr-$^8$Ser-$^9$Asp-$^{10}$Val-$^{11}$Ser-$^{12}$Ser-$^{13}$Tyr-$^{14}$Leu-$^{15}$Glu-$^{16}$Gly-$^{17}$Gln-$^{18}$Ala-$^{19}$Ala-$^{20}$Lys(Pal-γ-Glu)-$^{21}$Gly-$^{22}$Phe-$^{23}$Ile-$^{24}$Ala-$^{25}$Trp-$^{26}$Leu-$^{27}$Val-$^{28}$Arg-$^{29}$Gly-$^{30}$Arg-$^{31}$Gly-OH (residues 6-31 of SEQ ID NO: 6) or 3: H-$^{12}$Ser-$^{13}$Tyr-$^{14}$Leu-$^{15}$Glu-$^{16}$Gly-$^{17}$Gln-$^{18}$Ala-$^{19}$Ala-$^{20}$Lys(Pal-γ-Glu)-$^{21}$Glu-$^{22}$Phe-$^{23}$Ile-$^{24}$Ala-$^{25}$Trp-$^{26}$Leu-$^{27}$Val-$^{28}$Arg-$^{29}$Gly-$^{30}$Arg-$^{31}$Gly-OH (residues 12-31 of SEQ ID NO: 6)) were dissolved in 950 µL water. To this mixture, 50 µL 1M tricine buffer pH 9.0 was added and the pH was adjusted to 8.1 using a 3M NaOH solution. Subsequently, 10 µL of TCEP solution (100 mg/mL in water) and 100 µL of ligase (according to SEQ ID NO: 3) solution (10 mg/mL) were added. The mixture was left to react at ambient temperature. Every 15 minutes, 10 µL of the reaction mixture was withdrawn and quenched in 980 µL 5 vol % MSA in acetonitrile/water (2/1, v/v) and analysed using LC-MS.

After 180 minutes, the Cam-ester starting material had been consumed for each of the three reactions. Samples of the resultant product mixture were analyzed and the product and hydrolysis peaks were integrated. The ligation product for 1: was 72 area %, for 2:53 area % and for 3:95 area %.

SEQUENCES
SEQ ID NO 1: wild type gene encoding for
subtilisin BPN' amino acids -107 to 275
ENA|K02496|K02496.1 B. Subtilisin BPN'
Bacillus amyloliquefaciens
GTGAGAGGCAAAAAAGTATGGATCAGTTTGCTGTTTGCTTTAGCGTTAAT

CTTTTACGATGGCGTTCGGCAGCACATCCTCTGCCCAGGCGGCAGGGAAAT

CAAACGGGGAAAAGAAATATATTGTCGGGTTTAAACAGACAATGAGCACG

ATGAGCGCCGCTAAGAAGAAAGATGTCATTTCTGAAAAAGGCGGGAAAGT

GCAAAAGCAATTCAAATATGTAGACGCAGCTTCAGCTACATTAAACGAAA

AAGCTGTAAAAGAATTGAAAAAAGACCCGAGCGTCGCTTACGTTGAAGAA

GATCACGTAGCACATGCGTACGCGCAGTCCGTGCCTTACGGCGTATCACA

AATTAAAGCCCCTGCTCTGCACTCTCAAGGCTACACTGGATCAAATGTTA

AAGTAGCGGTTATCGACAGCGGTATCGATTCTTCTCATCCTGATTTAAAG

GTAGCAGGCGGAGCCAGCATGGTTCCTTCTGAAACAAATCCTTTCCAAGA

CAACAACTCTCACGGAACTCACGTTGCCGGCACAGTTGCGGCTCTTAATA

ACTCAATCGGTGTATTAGGCGTTGCGCCAAGCGCATCACTTTACGCTGTA

AAAGTTCTCGGTGCTGACGGTTCCGGCCAATACAGCTGGATCATTAACGG

AATCGAGTGGGCGATCGCAAACAATATGGACGTTATTAACATGAGCCTCG

GCGGACCTTCTGGTTCTGCTGCTTTAAAAGCGGCAGTTGATAAAGCCGTT

GCATCCGGCGTCGTAGTCGTTGCGGCAGCCGGTAACGAAGGCACTTCCGG

CAGCTCAAGCACAGTGGGCTACCCTGGTAAATACCCTTCTGTCATTGCAG

TAGGCGCTGTTGACAGCAGCAACCAAAGAGCATCTTTCTCAAGCGTAGGA

CCTGAGCTTGATGTCATGGCACCTGGCGTATCTATCCAAAGCACGCTTCC

TGGAAACAAATACGGGGCGTACAACGGTACGTCAATGGCATCTCCGCACG

TTGCCGGAGCGGCTGCTTTGATTCTTTCTAAGCACCCGAACTGGACAAAC

ACTCAAGTCCGCAGCAGTTTAGAAAACACCACTACAAAACTTGGTGATTC

TTTCTACTATGGAAAAGGGCTGATCAACGTACAGGCGGCAGCTCAGTAA

SEQ ID NO 2: wild type subtilisin BPN' (mature)
>SUBT_BACAM Subtilisin BPN' Bacillus
amyloliquefaciens mature 1 to 275
>sp|P00782|108-382
AQSVPYGVSQIKAPALHSQGYTGSNVKVAVIDSGIDSSHPDLKVAGGASM

VPSETNPFQDNNSHGTHVAGTVAALNNSIGVLGVAPSASLYAVKVLGADG

SGQYSWIINGIEWAIANNMDVINMSLGGPSGSAALKAAVDKAVASGVVVV

AAAGNEGTSGSSSTVGYPGKYPSVIAVGAVDSSNQRASFSSVGPELDVMA

PGVSIQSTLPGNKYGAYNGTSMASPHVAGAAALILSKHPNWTNTQVRSSL

ENTTTKLGDSFYYGKGLINVQAAAQ

SEQ ID NO 3: subtilisin BPN' variant having
mutations Q2K, S3C,P5S, S9A,I31L, K43N, M50F,
N62A, A73L, A75-83, E156N, G166E, G169A, S188P,
F189W, Q206C, N212G, Y217H, N218D, S221C, M222P,
P225N, T254A, and Q271E and a His tag
AKCVSYGVAQIKAPALHSQGYTGSNVKVAVLDSGIDSSHPDLNVAGGASF

VPSETNPFQDNASHGTHVAGTVLAVAPSASLYAVKVLGADGSGQYSWIIN

GIEWAIANNMDVINMSLGGPSGSAALKAAVDKAVASGVVVVAAAGNNGTS

GSSSTVEYPAKYPSVIAVGAVDSSNQRAPWSSVGPELDVMAPGVSICSTL

PGGKYGAHDGTCPASNHVAGAAALILSKHPNWTNTQVRSSLENTATKLGD

SFYYGKGLINVEAAAQHHHHHH

-continued

SEQ ID NO 14: subtilisin BPN' variant having
mutations Q2K, S3C, P5S, S9A,I31L, K43N, M50F,
A73L, Δ75-83, E156S, G166S, G169A, S188P, Q206C,
N212G, Y217H, S221C, M222P, P225N, T254A, and
Q271E and a His tag
AKCVSYGVAQIKAPALHSQGYTGSNVKVAVLDSGIDSSHPDLNVAGGASF
VPSETNPFQDNNSHGTHVAGTVLAVAPSASLYAVKVLGADGSGQYSWIIN
GIEWAIANNMDVINMSLGGPSGSAALKAAVDKAVASGVVVVAAAGNSGTS
GSSSTVSYPAKYPSVIAVGAVDSSNQRAPFSSVGPELDVMAPGVSICSTL
PGGKYGAHSGTCPASNHVAGAAALILSKHPNWTNTQVRSSLENTATKLGD
SFYYGKGLINVEAAAQHHHHHH

The invention claimed is:

1. A method for synthesising a peptide comprising the sequence His-X-Glu-Gly-Thr-Phe-Thr-Ser-Asp-Val-Ser-Ser-Tyr-Leu-Glu-Gly-Gln-Ala-Ala-Y-Glu-Phe-Ile-Ala-Trp-Leu-Val-Z-Gly-Arg-Gly, comprising enzymatically coupling (a) a peptide C-terminal ester or thioester comprising a first peptide fragment comprising the sequence His-X-Glu-Gly-Thr-Phe-Thr-Ser-Asp-Val-Ser-(thio)ester (SEQ ID NO: 11); and (b) a peptide nucleophile having an N-terminally unprotected amine comprising a second peptide fragment comprising the sequence H-Ser-Tyr-Leu-Glu-Gly-Gln-Ala-Ala-Y-Glu-Phe-Ile-Ala-Trp-Leu-Val-Z-Gly-Arg-Gly (SEQ ID NO: 12)

wherein

X is Ala or an α-amino-isobutyric acid (Aib) residue;

Y is Lys, which Lys has a free side-chain ε-amino group or of which Lys the side-chain ε-amino group is protected with a protective group or of which Lys the side-chain ε-amino group is functionalized with an amino acid or another functional group selected from the group consisting of γ-Glu-OH, Pal-γ-Glu-OH, AEEA-AEEA-γ-Glu-OH and AEEA-AEEA-γ-Glu-N-17-carboxyheptadecanoyl-OH, wherein Pal is palmitoyl and AEEA-AEEA is -2-[2-(2-aminoethoxy)ethoxy]acetyl-2-[2-(2-aminoethoxy)ethoxy]acetyl; and Z is Arg or Lys;

which enzymatic coupling is catalysed by a ligase, wherein the ligase is a subtilisin BPN' variant or a homologue thereof, which comprises the following mutations compared to subtilisin BPN' represented by SEQ ID NO: 2:

a deletion of the amino acids corresponding to positions 75-83;

a mutation at the amino acid position corresponding to S221, the mutation being S221C or S221 selenocysteine;

wherein the amino acid positions are defined according to the sequence of subtilisin BPN' represented by SEQ ID NO:2.

2. The method according to claim 1, wherein the peptide that is synthesized is Liraglutide.

3. The method according to claim 2, comprising the enzymatic coupling, catalysed by the ligase, of a) the peptide C-terminal ester or thioester comprising the sequence His-Ala-Glu-Gly-Thr-Phe-Thr-Ser-Asp-Val-Ser-(thio)ester (SEQ ID NO: 11), and b) the peptide nucleophile comprising the sequence H-Ser-Tyr-Leu-Glu-Gly-Gln-Ala-Ala-Y-Glu-Phe-Ile-Ala-Tip-Leu-Val-Arg-Gly-Arg-Gly (SEQ ID NO: 12), wherein Y is Lys(Pal-γ-Glu-OH).

4. The method according to claim 2, comprising the enzymatic coupling catalysed by the ligase of a) the peptide C-terminal ester or thioester represented by the formula P—W$_y$-His-Ala-Glu-Gly-Thr-Phe-Thr-Ser-Asp-Val-Ser-(thio)ester (SEQ ID NO: 11), wherein P is a protective group, v is an integer having a value of at least 0, and each W independently represents the same or a different amino acid residue, and
b) the peptide nucleophile comprising the sequence H-Ser-Tyr-Leu-Glu-Gly-Gln-Ala-Ala-Lys(γ-Glu-OH)-Glu-Phe-Ile-Ala-Trp-Leu-Val-Arg-Gly-Arg-Gly (SEQ ID NO: 12); and thereafter providing said Lys(γ-Glu-OH) with a palmitoyl group (Pal).

5. The method according to claim 4, wherein v is an integer having a value of 1-5.

6. The method according to claim 5, wherein v is an integer having a value of 1-3.

7. The method according to claim 6, wherein v is 1.

8. The method according to claim 2, comprising the enzymatic coupling catalysed by the ligase of
a) the peptide C-terminal ester or thioester comprising the sequence His-Ala-Glu-Gly-Thr-Phe-Thr-Ser-Asp-Val-Ser-(thio)ester (SEQ ID NO: 11), and
b) the peptide nucleophile comprising the sequence H-Ser-Tyr-Leu-Glu-Gly-Gln-Ala-Ala-Y-Glu-Phe-Ile-Ala-Trp-Leu-Val-Arg-Gly-Arg-Gly (SEQ ID NO: 12), wherein Y is a lysine residue having a free ε-amino side chain; and thereafter providing said amino side chain with Pal-γ-Glu-OH.

9. The method according to claim 1, wherein the peptide that is synthesized is Semaglutide.

10. The method according to claim 9, comprising the enzymatic coupling—catalysed by the ligase—of
a) the peptide C-terminal ester or thioester comprising the sequence His-Aib-Glu-Gly-Thr-Phe-Thr-Ser-Asp-Val-Ser-(thio)ester (SEQ ID NO: 11), and
b) the peptide nucleophile comprising the sequence H-Ser-Tyr-Leu-Glu-Gly-Gln-Ala-Ala-Y-Glu-Phe-Ile-Ala-Trp-Leu-Val-Arg-Gly-Arg-Gly (SEQ ID NO: 12), wherein Y is Lys(AEEA-AEEA-γ-Glu-N-17-carboxyheptadecanoyl-OH).

11. The method according to claim 9, comprising the enzymatic coupling—catalysed by the ligase—of
a) the peptide C-terminal ester or thioester represented by the formula P—W$_v$-His-Aib-Glu-Gly-Thr-Phe-Thr-Ser-Asp-Val-Ser-(thio)ester (SEQ ID NO: 11),
wherein P is a protective group, v is an integer having a value of at least 0, and each W independently represents the same or a different amino acid residue, and
b) the peptide nucleophile comprising the sequence H-Ser-Tyr-Leu-Glu-Gly-Gln-Ala-Ala-Y-Glu-Phe-Ile-Ala-Trp-Leu-Val-Arg-Gly-Arg-Gly (SEQ ID NO: 12), wherein Y is Lys(AEEA-AEEA-γ-Glu-OH), and thereafter
providing the Lys(AEEA-AEEA-γ-Glu-OH) with a 17-carboxyheptadecanoyl group.

12. The method according to claim 11, wherein v is an integer having a value of 1-5.

13. The method according to claim 12, wherein v is an integer having a value of 1-3.

14. The method according to claim 13, wherein v is 1.

15. The method according to claim 9, comprising the enzymatic coupling—catalysed by the ligase—of
a) the peptide C-terminal ester or thioester comprising the sequence His-Aib-Glu-Gly-Thr-Phe-Thr-Ser-Asp-Val-Ser-(thio)ester (SEQ ID NO: 11), and
b) the peptide nucleophile comprising the sequence H-Ser-Tyr-Leu-Glu-Gly-Gln-Ala-Ala-Y-Glu-Phe-Ile-Ala-Trp-Leu-Val-Arg-Gly-Arg-Gly (SEQ ID NO: 12), wherein Y is a lysine residue having a free side chain, and thereafter providing the ε-amino side chain of the Lys with an AEEA-AEEA-γ-Glu-N-17-carboxyheptadecanoyl-OH group.

16. The method according to claim 1, wherein the peptide that is synthesized is GLP-1.

17. The method according to claim 1, wherein the ligase comprises 1-13 further mutations selected from the group of mutations at an amino acid position corresponding to Q2, S3, P5, S9, I31, K43, M50, A73, S188, Q206, N212, T254 and Q271 of SEQ ID NO: 2, wherein one or more of said mutations are selected from the group consisting of Q2K, S3C, P5S, S9A, I31L, K43N, M50F, A73L, S188P, Q206C, N212G, T254A and Q271E.

18. The method according to claim 1, wherein the (thio)ester of the peptide C-terminal ester or thioester is a Cam-AA1-AA2-ester, wherein AA1 represents an alanine, valine, leucine, isoleucine, phenylalanine, methionine or tryptophan unit with an unprotected side-chain functionality, and AA2 represents an arginine or lysine unit with an unprotected side-chain functionality.

19. The method according to claim 17, wherein the ligase is a subtilisin BPN' variant with SEQ ID NO: 3 comprising the mutations Q2K, S3C, P5S, S9A, I31L, K43N, M50F, N62A, A73L, Δ75-83, E156N, G166E, G169A, S188P, F189W, Q206C, N212G, Y217H, N218D, S221C, M222P, P225N, T254A, Q271E or a subtilisin BPN' variant with SEQ ID NO: 14 comprising the mutations Q2K, S3C, P5S, S9A, I31L, K43N, M50F, A73L, Δ75-83, E156S, G166S, G169A, S188P, Q206C, N212G, Y217H, S221C, M222P, P225N, T254A, and Q271E or a homologue thereof comprising respectively said mutations and having at least 80%, or 95%, sequence identity, and optionally comprising a His tag.

20. The method according to claim 1, wherein the subtilisin BPN' variant or a homologue thereof further comprises a mutation at the amino acid position corresponding to P225.

21. The method according to claim 17, wherein the ligase comprises 8-11 further mutations selected from the group of mutations at an amino acid position corresponding to Q2, S3, P5, S9, I31, K43, M50, A73, S188, Q206, N212, T254 and Q271 of SEQ ID NO: 2, wherein one or more of said mutations are selected from the group consisting of Q2K, S3C, P5S, S9A, I31L, K43N, M50F, A73L, S188P, Q206C, N212G, T254A and Q271E.

* * * * *

SEQUENCE LISTING

<160> NUMBER OF SEQ ID NOS: 14

<210> SEQ ID NO 1
<211> LENGTH: 1149
<212> TYPE: DNA
<213> ORGANISM: Bacillus amyloliquefaciens
<220> FEATURE:
<221> NAME/KEY: CDS
<222> LOCATION: (322)..(1149)

<400> SEQUENCE: 1
gtgagaggca aaaaagtatg gatcagtttg ctgtttgctt tagcgttaat ctttacgatg      60
gcgttcggca gcacatcctc tgcccaggcg gcagggaaat caaacgggga aagaaatat     120 attgtcgggt ttaaacagac aatgagcacg atgagcgccg ctaagaagaa agatgtcatt    180
tctgaaaaag gcgggaaagt gcaaaagcaa ttcaaatatg tagacgcagc ttcagctaca    240
ttaaacgaaa aagctgtaaa agaattgaaa aagacccga gcgtcgctta cgttgaagaa     300
gatcacgtag cacatgcgta c gcg cag tcc gtg cct tac ggc gta tca caa      351
                        Ala Gln Ser Val Pro Tyr Gly Val Ser Gln
                         1               5                  10 att aaa gcc cct gct ctg cac tct caa ggc tac act gga tca aat gtt      399
Ile Lys Ala Pro Ala Leu His Ser Gln Gly Tyr Thr Gly Ser Asn Val
             15                  20                  25 aaa gta gcg gtt atc gac agc ggt atc gat tct tct cat cct gat tta      447
Lys Val Ala Val Ile Asp Ser Gly Ile Asp Ser Ser His Pro Asp Leu
         30                  35                  40 aag gta gca ggc gga gcc agc atg gtt cct tct gaa aca aat cct ttc      495
Lys Val Ala Gly Gly Ala Ser Met Val Pro Ser Glu Thr Asn Pro Phe
     45                  50                  55 caa gac aac aac tct cac gga act cac gtt gcc ggc aca gtt gcg gct      543
Gln Asp Asn Asn Ser His Gly Thr His Val Ala Gly Thr Val Ala Ala
 60                  65                  70 ctt aat aac tca atc ggt gta tta ggc gtt gcg cca agc gca tca ctt      591
Leu Asn Asn Ser Ile Gly Val Leu Gly Val Ala Pro Ser Ala Ser Leu
75                  80                  85                  90 tac gct gta aaa gtt ctc ggt gct gac ggt tcc ggc caa tac agc tgg      639
Tyr Ala Val Lys Val Leu Gly Ala Asp Gly Ser Gly Gln Tyr Ser Trp
                 95                 100                 105 atc att aac gga atc gag tgg gcg atc gca aac aat atg gac gtt att      687
Ile Ile Asn Gly Ile Glu Trp Ala Ile Ala Asn Asn Met Asp Val Ile
             110                 115                 120 aac atg agc ctc ggc gga cct tct ggt tct gct gct tta aaa gcg gca      735
Asn Met Ser Leu Gly Gly Pro Ser Gly Ser Ala Ala Leu Lys Ala Ala
         125                 130                 135 gtt gat aaa gcc gtt gca tcc ggc gtc gta gtc gtt gcg gca gcc ggt      783
Val Asp Lys Ala Val Ala Ser Gly Val Val Val Val Ala Ala Ala Gly
     140                 145                 150 aac gaa ggc act tcc ggc agc tca agc aca gtg ggc tac cct ggt aaa      831
Asn Glu Gly Thr Ser Gly Ser Ser Ser Thr Val Gly Tyr Pro Gly Lys
 155                 160                 165                 170

-continued

| | | |
|---|---|---|
| tac cct tct gtc att gca gta ggc gct gtt gac agc agc aac caa aga<br>Tyr Pro Ser Val Ile Ala Val Gly Ala Val Asp Ser Ser Asn Gln Arg<br>                   175                                180                         185 | | 879 |
| gca tct ttc tca agc gta gga cct gag ctt gat gtc atg gca cct ggc<br>Ala Ser Phe Ser Ser Val Gly Pro Glu Leu Asp Val Met Ala Pro Gly<br>                 190                            195                            200 | | 927 |
| gta tct atc caa agc acg ctt cct gga aac aaa tac ggg gcg tac aac<br>Val Ser Ile Gln Ser Thr Leu Pro Gly Asn Lys Tyr Gly Ala Tyr Asn<br>                 205                            210 | | 975 |
| ggt acg tca atg gca tct ccg cac gtt gcc gga gcg gct gct ttg att<br>Gly Thr Ser Met Ala Ser Pro His Val Ala Gly Ala Ala Ala Leu Ile<br>220                                225                            230 | | 1023 |
| ctt tct aag cac ccg aac tgg aca aac act caa gtc cgc agc agt tta<br>Leu Ser Lys His Pro Asn Trp Thr Asn Thr Gln Val Arg Ser Ser Leu<br>235                             240                        245                        250 | | 1071 |
| gaa aac acc act aca aaa ctt ggt gat tct ttc tac tat gga aaa ggg<br>Glu Asn Thr Thr Thr Lys Leu Gly Asp Ser Phe Tyr Tyr Gly Lys Gly<br>                 255                            260                        265 | | 1119 |
| ctg atc aac gta cag gcg gca gct cag taa<br>Leu Ile Asn Val Gln Ala Ala Ala Gln<br>                 270                            275 | | 1149 |

<210> SEQ ID NO 2
<211> LENGTH: 275
<212> TYPE: PRT
<213> ORGANISM: Bacillus amyloliquefaciens

<400> SEQUENCE: 2

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
    210                 215                 220

```
Pro His Val Ala Gly Ala Ala Leu Ile Leu Ser Lys His Pro Asn
225                 230                 235                 240

Trp Thr Asn Thr Gln Val Arg Ser Ser Leu Glu Asn Thr Thr Thr Lys
            245                 250                 255

Leu Gly Asp Ser Phe Tyr Tyr Gly Lys Gly Leu Ile Asn Val Gln Ala
            260                 265                 270

Ala Ala Gln
        275

<210> SEQ ID NO 3
<211> LENGTH: 272
<212> TYPE: PRT
<213> ORGANISM: Artificial Sequence
<220> FEATURE:
<223> OTHER INFORMATION: mutant subtilisin B
<220> FEATURE:
<221> NAME/KEY: MISC_FEATURE
<222> LOCATION: (267)..(272)
<223> OTHER INFORMATION: His-tag

<400> SEQUENCE: 3

Ala Lys Cys Val Ser Tyr Gly Val Ala Gln Ile Lys Ala Pro Ala Leu
1               5                   10                  15

His Ser Gln Gly Tyr Thr Gly Ser Asn Val Lys Val Ala Val Leu Asp
            20                  25                  30

Ser Gly Ile Asp Ser Ser His Pro Asp Leu Asn Val Ala Gly Gly Ala
        35                  40                  45

Ser Phe Val Pro Ser Glu Thr Asn Pro Phe Gln Asp Asn Ala Ser His
    50                  55                  60

Gly Thr His Val Ala Gly Thr Val Leu Ala Val Ala Pro Ser Ala Ser
65                  70                  75                  80

Leu Tyr Ala Val Lys Val Leu Gly Ala Asp Gly Ser Gly Gln Tyr Ser
                85                  90                  95

Trp Ile Ile Asn Gly Ile Glu Trp Ala Ile Ala Asn Asn Met Asp Val
            100                 105                 110

Ile Asn Met Ser Leu Gly Gly Pro Ser Gly Ser Ala Ala Leu Lys Ala
        115                 120                 125

Ala Val Asp Lys Ala Val Ala Ser Gly Val Val Val Val Ala Ala Ala
    130                 135                 140

Gly Asn Asn Gly Thr Ser Gly Ser Ser Ser Thr Val Glu Tyr Pro Ala
145                 150                 155                 160

Lys Tyr Pro Ser Val Ile Ala Val Gly Ala Val Asp Ser Ser Asn Gln
                165                 170                 175

Arg Ala Pro Trp Ser Ser Val Gly Pro Glu Leu Asp Val Met Ala Pro
            180                 185                 190

Gly Val Ser Ile Cys Ser Thr Leu Pro Gly Gly Lys Tyr Gly Ala His
        195                 200                 205

Asp Gly Thr Cys Pro Ala Ser Asn His Val Ala Gly Ala Ala Ala Leu
    210                 215                 220

Ile Leu Ser Lys His Pro Asn Trp Thr Asn Thr Gln Val Arg Ser Ser
225                 230                 235                 240

Leu Glu Asn Thr Ala Thr Lys Leu Gly Asp Ser Phe Tyr Tyr Gly Lys
                245                 250                 255

Gly Leu Ile Asn Val Glu Ala Ala Ala Gln His His His His His His
            260                 265                 270

<210> SEQ ID NO 4
```

```
<211> LENGTH: 31
<212> TYPE: PRT
<213> ORGANISM: Artificial Sequence
<220> FEATURE:
<223> OTHER INFORMATION: consensus peptide fragment
<220> FEATURE:
<221> NAME/KEY: VARIANT
<222> LOCATION: (2)..(2)
<223> OTHER INFORMATION: may also be an alpha-amino-isobutyric acid unit
<220> FEATURE:
<221> NAME/KEY: MISC_FEATURE
<222> LOCATION: (20)..(20)
<223> OTHER INFORMATION: Lys has a free side-chain epsilon-amino group
      or  a  side-chain epsilon-amino group that is protected with a
      protective group or a side-chain epsilon-amino group that is
      functionalised with an amino acid or another functional group
<220> FEATURE:
<221> NAME/KEY: VARIANT
<222> LOCATION: (28)..(28)
<223> OTHER INFORMATION: may also be K

<400> SEQUENCE: 4

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 5
<211> LENGTH: 31
<212> TYPE: PRT
<213> ORGANISM: Homo sapiens

<400> SEQUENCE: 5

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 6
<211> LENGTH: 31
<212> TYPE: PRT
<213> ORGANISM: Homo sapiens
<220> FEATURE:
<221> NAME/KEY: MOD_RES
<222> LOCATION: (20)..(20)
<223> OTHER INFORMATION: Lys is Lys(Pal-gamma-Glu)-
<220> FEATURE:
<221> NAME/KEY: MOD_RES
<222> LOCATION: (20)..(20)
<223> OTHER INFORMATION: Lys is Lys(Pal-gamma-Glu)

<400> SEQUENCE: 6

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 7
<211> LENGTH: 31
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: bAib
<220> FEATURE:
<221> NAME/KEY: MOD_RES
<222> LOCATION: (20)..(20)
<223> OTHER INFORMATION: Lys is Lys(AEEA-AEEA-gamma-Glu-17-
      carboxyheptadecanoyl)
```

```
<400> SEQUENCE: 7

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 8
<211> LENGTH: 27
<212> TYPE: PRT
<213> ORGANISM: Artificial Sequence
<220> FEATURE:
<223> OTHER INFORMATION: coupling reagent for production of liraglutide
<220> FEATURE:
<221> NAME/KEY: MOD_RES
<222> LOCATION: (20)..(20)
<223> OTHER INFORMATION: Lys is Lys(Pal-Glu-OX) in which X is H or
      protective group

<400> SEQUENCE: 8

Thr Phe Thr Ser Asp Val Ser Ser Tyr Leu Glu Gly Gln Ala Ala Lys
1               5                   10                  15

Glu Phe Ile Ala Trp Leu Val Arg Gly Arg Gly
            20                  25

<210> SEQ ID NO 9
<211> LENGTH: 14
<212> TYPE: PRT
<213> ORGANISM: Artificial Sequence
<220> FEATURE:
<223> OTHER INFORMATION: 13-mer C-terminal ester for coupling
<220> FEATURE:
<221> NAME/KEY: MOD_RES
<222> LOCATION: (14)..(14)
<223> OTHER INFORMATION: is OCam-Leu

<400> SEQUENCE: 9

His Ala Glu Gly Thr Phe Thr Ser Asp Val Ser Ser Tyr Leu
1               5                   10

<210> SEQ ID NO 10
<211> LENGTH: 18
<212> TYPE: PRT
<213> ORGANISM: Artificial Sequence
<220> FEATURE:
<223> OTHER INFORMATION: 18-mer coupling peptide

<400> SEQUENCE: 10

Leu Glu Gly Gln Ala Ala Lys Glu Phe Ile Ala Trp Leu Val Arg Gly
1               5                   10                  15

Arg Gly

<210> SEQ ID NO 11
<211> LENGTH: 11
<212> TYPE: PRT
<213> ORGANISM: Artificial Sequence
<220> FEATURE:
<223> OTHER INFORMATION: 11-mer coupling peptide
<220> FEATURE:
<221> NAME/KEY: VARIANT
<222> LOCATION: (2)..(2)
<223> OTHER INFORMATION: may also be an alpha-amino-isobutyric acid unit
<220> FEATURE:
<221> NAME/KEY: MOD_RES
<222> LOCATION: (11)..(11)
<223> OTHER INFORMATION: thioester

<400> SEQUENCE: 11
```

```
His Ala Glu Gly Thr Phe Thr Ser Asp Val Ser
1               5                  10

<210> SEQ ID NO 12
<211> LENGTH: 20
<212> TYPE: PRT
<213> ORGANISM: Artificial Sequence
<220> FEATURE:
<223> OTHER INFORMATION: 20-mer coupling peptide
<220> FEATURE:
<221> NAME/KEY: MISC_FEATURE
<222> LOCATION: (9)..(9)
<223> OTHER INFORMATION: Lys has a free side-chain epsilon-amino group
      or a side-chain epsilon-amino group that is protected with a
      protective group or a side-chain epsilon-amino group that is
      functionalised with an amino acid or another functional group
<220> FEATURE:
<221> NAME/KEY: MOD_RES
<222> LOCATION: (17)..(17)
<223> OTHER INFORMATION: May also by Lys

<400> SEQUENCE: 12

Ser Tyr Leu Glu Gly Gln Ala Ala Lys Glu Phe Ile Ala Trp Leu Val
1               5                   10                  15

Arg Gly Arg Gly
            20

<210> SEQ ID NO 13
<211> LENGTH: 20
<212> TYPE: PRT
<213> ORGANISM: Artificial Sequence
<220> FEATURE:
<223> OTHER INFORMATION: 20-mer coupling peptide
<220> FEATURE:
<221> NAME/KEY: MOD_RES
<222> LOCATION: (9)..(9)
<223> OTHER INFORMATION: Lys(Pal- gamma -Glu-OH)
<220> FEATURE:
<221> NAME/KEY: MOD_RES
<222> LOCATION: (9)..(9)
<223> OTHER INFORMATION: Lys(Pal- gamma -Glu-OH) or Lys(gamma -Glu-OH)

<400> SEQUENCE: 13

Ser Tyr Leu Glu Gly Gln Ala Ala Lys Glu Phe Ile Ala Trp Leu Val
1               5                   10                  15

Arg Gly Arg Gly
            20

<210> SEQ ID NO 14
<211> LENGTH: 272
<212> TYPE: PRT
<213> ORGANISM: artificial sequence
<220> FEATURE:
<223> OTHER INFORMATION: mutant subtilisin B
<220> FEATURE:
<221> NAME/KEY: MISC_FEATURE
<222> LOCATION: (267)..(272)
<223> OTHER INFORMATION: His-tag

<400> SEQUENCE: 14

Ala Lys Cys Val Ser Tyr Gly Val Ala Gln Ile Lys Ala Pro Ala Leu
1               5                   10                  15

His Ser Gln Gly Tyr Thr Gly Ser Asn Val Lys Val Ala Val Leu Asp
                20                  25                  30

Ser Gly Ile Asp Ser Ser His Pro Asp Leu Asn Val Ala Gly Gly Ala
            35                  40                  45

Ser Phe Val Pro Ser Glu Thr Asn Pro Phe Gln Asp Asn Asn Ser His
```

-continued

```
                50                  55                  60
Gly Thr His Val Ala Gly Thr Val Leu Ala Val Ala Pro Ser Ala Ser
 65              70                  75                  80

Leu Tyr Ala Val Lys Val Leu Gly Ala Asp Gly Ser Gly Gln Tyr Ser
             85                  90                  95

Trp Ile Ile Asn Gly Ile Glu Trp Ala Ile Ala Asn Asn Met Asp Val
             100                 105                 110

Ile Asn Met Ser Leu Gly Gly Pro Ser Gly Ser Ala Ala Leu Lys Ala
         115                 120                 125

Ala Val Asp Lys Ala Val Ala Ser Gly Val Val Val Val Ala Ala Ala
         130                 135                 140

Gly Asn Ser Gly Thr Ser Gly Ser Ser Ser Thr Val Ser Tyr Pro Ala
 145                 150                 155                 160

Lys Tyr Pro Ser Val Ile Ala Val Gly Ala Val Asp Ser Ser Asn Gln
             165                 170                 175

Arg Ala Pro Phe Ser Ser Val Gly Pro Glu Leu Asp Val Met Ala Pro
             180                 185                 190

Gly Val Ser Ile Cys Ser Thr Leu Pro Gly Gly Lys Tyr Gly Ala His
         195                 200                 205

Ser Gly Thr Cys Pro Ala Ser Asn His Val Ala Gly Ala Ala Ala Leu
 210                 215                 220

Ile Leu Ser Lys His Pro Asn Trp Thr Asn Thr Gln Val Arg Ser Ser
225                  230                 235                 240

Leu Glu Asn Thr Ala Thr Lys Leu Gly Asp Ser Phe Tyr Tyr Gly Lys
             245                 250                 255

Gly Leu Ile Asn Val Glu Ala Ala Gln His His His His His His
             260                 265                 270
```